(12) United States Patent
Chan et al.

(10) Patent No.: US 8,168,801 B2
(45) Date of Patent: May 1, 2012

(54) IMIDAZOLIUM-TYPE IONIC OLIGOMERS

(75) Inventors: Tak-Hang Chan, Montreal (CA); Xun He, Hockessin, DE (US)

(73) Assignees: The Royal Institution for the Advancement of Learning/McGill University, Montreal (CA); The Hong Kong Polytechnic University, Kowloon (HK)

( * ) Notice: Subject to any disclaimer, the term of this patent is extended or adjusted under 35 U.S.C. 154(b) by 236 days.

(21) Appl. No.: 12/530,890

(22) PCT Filed: Mar. 12, 2008

(86) PCT No.: PCT/CA2008/000489
§ 371 (c)(1),
(2), (4) Date: Sep. 11, 2009

(87) PCT Pub. No.: WO2008/110007
PCT Pub. Date: Sep. 18, 2008

(65) Prior Publication Data
US 2010/0093975 A1 Apr. 15, 2010

Related U.S. Application Data

(60) Provisional application No. 60/906,212, filed on Mar. 12, 2007.

(51) Int. Cl.
*C07D 403/06* (2006.01)
*C07D 403/14* (2006.01)
(52) U.S. Cl. .................................................. 548/313.7
(58) Field of Classification Search ............... 548/313.7
See application file for complete search history.

(56) References Cited

OTHER PUBLICATIONS

Wong et al. Org. Biomol. Chem. 2005, 3(23), 4201-4208.*
Viciano et al. Organometallics 2006, 25, 1120-1134.*

* cited by examiner

*Primary Examiner* — Jason M Nolan
(74) *Attorney, Agent, or Firm* — Fulbright & Jaworski L.L.P.

(57) ABSTRACT

The present disclosure relates to structurally defined imidazolium-type ionic oligomers of the formula:

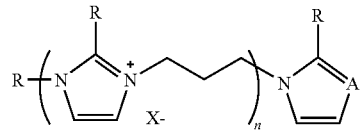

wherein n is an integer ranging from 1 to 20; A is N or

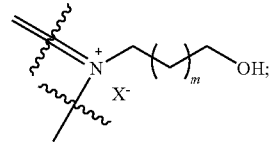

m is an integer ranging from 1 to 5; X is selected from the group consisting of Br, OTf, $CF_3CO_2$, $CH_3CO_2$, $BF_4$, $PF_6$, $NTf_2$, F, Cl and I; and R is selected from the group consisting of hydrogen and $C_{1-10}$ alkyl. The imidazolium-type ionic oligomers lend themselves as soluble/solid supports for biopolymer synthesis.

14 Claims, No Drawings

IMIDAZOLIUM-TYPE IONIC OLIGOMERS

CROSS REFERENCE TO RELATED APPLICATIONS

The present application is a national phase application under 35 U.S.C. §371 of International Patent Application PCT Application No. PCT/CA2008/000489, filed Mar. 12, 2008, which claims the benefit of U.S. Provisional Application No. 60/906,212, filed Mar. 12, 2007. The entire contents of these applications are incorporated by reference.

FIELD OF THE INVENTION

The present disclosure relates to imidazolium-type ionic oligomers. More specifically, but not exclusively, the present disclosure relates to structurally defined imidazolium-type ionic oligomers as soluble/solid support for biopolymer synthesis.

BACKGROUND OF THE INVENTION

The efficient synthesis of oligopeptides represents a contemporary challenge which has led to the development of several novel synthetic approaches. Since Merrifield introduced the use of polystyrene supports for the synthesis of oligopeptides, insoluble supports have become an indispensable tool in solid phase synthesis, especially in the synthesis of biopolymers such as polypeptides of variable length.[1,2] A notable advantage of solid phase synthesis is the relative simple purification cycle, comprising the removal of excess reagents and soluble side products by simple filtration. The target product remains anchored to the solid support. The product is readily removed from the solid support and isolated by filtration. The entire process is amenable to automation. Although widely practiced in the art, solid phase synthesis retains some of the drawbacks that are typically associated with heterogeneous reaction conditions such as non-linear reaction kinetics, unequal distribution of and/or access to the reaction sites, solvation problems, and inefficient coupling rates which often necessitate a large excess of reagents to drive the reactions to completion. Further drawbacks include the low loading capacity and high cost of the solid supports, making large scale synthesis of oligopeptides using such supports very expensive. Moreover, characterization of the support-bound growing oligopeptide intermediates by common analytical methods such as TLC, NMR and MS is not practical.

The need for alternative methodologies, with the aim of restoring homogeneous reaction conditions and overcoming some of the inherent disadvantages of solid phase synthesis, has led to the development of soluble polymer supports. In recent years, the use of soluble polymer supports has received considerable attention because such "liquid phase" synthesis retains the advantages of conventional solution chemistry, while still retaining the advantage of facilitated product purification. Soluble polyethylene glycol (PEG), polyvinyl alcohol and other polymers have all been successfully employed for the synthesis of oligopeptides.[3] Moreover, soluble polyethylene glycol (PEG) polymers have also been used as supports for small molecule synthesis.[4] However, the use of soluble polymer supports is still limited by low loading capacity, diminished solubility during the synthesis of longer peptides, low aqueous solubility, lack of solubility in ether solvents in addition to energy intensive cooling required for purification.

More recently, a new solution-phase synthesis method based on fluorinated (fluorous) soluble supports has been advocated.[5] The approach is based on the preferential solubility of the fluorous support and the fluorinated reagents in fluorous solvents (i.e. perfluoroalkanes). The non-fluorinated reagents can be readily separated from the product anchored to the fluorous support through fluorous-organic solvent partitioning[6a-d] or fluorous silica gel-based solid-phase extraction (SPE).[6e-h] However, this approach requires the use of fluorinated compounds, which are not generally readily available. Purification can be achieved through a temperature switch that causes a phase separation between the previously miscible fluorous solvent and the organic solvent, thus facilitating separation. The utility of fluorous phase methodology in organic synthesis has been demonstrated for the synthesis of oligopeptides[7] and small molecules.[5] The cost of perfluoroalkane solvents, the need for specialized fluorinated reagents and the energy cost associated with the temperature switch are potential limitations that limit broad application of fluorous phase organic synthesis.

Ionic liquids (ILs) have received considerable attention in recent years as environmentally benign reaction media for organic reactions.[8] Because of their characteristic chemical and physical properties such as non-flammability, high thermal and chemical stability, lack of a measurable vapor pressure, high loading capacity, high ionic conductivity[9] and electrochemical stability[10], ionic liquids have found acceptance in diverse areas such as organic catalysis,[8] electrochemical devices[11] and analytical chemistry.[12] Recently, ionic liquids have been used as soluble supports for catalysis,[13,14] reagents and soluble supports[15] supplementing the solid phase synthesis[1] or other solution-phase methodologies such as soluble-polymer supported synthesis[4] or fluorous phase synthesis.[5] Some enzymatic reactions, have also been carried out in ionic liquids.[16] Room temperature ionic liquids have also been widely explored as media for electrochemical technologies,[17] chemical extractions[18], and other industrial processes.[19]

Most ionic liquids comprise organic cations and inorganic anions. Non-limiting examples of ionic liquids include alkylimidazolium and pyridinium salts of halides, tetrafluoroborate and hexafluorophosphate. In most cases, ionic liquids can be readily recycled. By modifying the structure of the cation and/or the anion, the solubility of ionic liquids can be tuned so that they can phase separate from organic as well as aqueous media, thus facilitating separation and purification. Ionic liquids can thus serve as viable soluble functional supports in organic synthesis. The substrate solubility can also be tuned.[20] Recent reports have successfully demonstrated the utility of IL-supported synthesis (ILSS) of small molecules,[21,22,23] small peptides,[24] oligosaccharides[25] and oligonucleotides.[26] Ionic liquids have also been used as ion sources to make electronic materials,[27,28] fuel cells,[29] lithium batteries,[30] photoelectrochemical materials,[31] solar cells,[32] piezoelectric sensing materials for gas sensors[33], for the preparation of ionic liquid-cellulose composites,[34] supported ionic membranes,[35] nanoparticle stabilizing ligands,[36] $CO_2$ absorbents,[37] as well as analytical materials for chromatography 38,39, mass spectrometry,[40] and ion exchange absorbents.[41]

IL-supported synthesis possesses most of the advantages common to solution-phase syntheses because the reactions are conducted in a substantially homogenous phase. Since the IL-bound molecules are usually highly soluble in polar organic solvents (solvents in which the reactions are conducted), but generally insoluble in less polar or non-polar solvents such as ethyl acetate, ethers and alkanes, the IL-bound species can be readily phase-separated by the addition of the less polar solvent into the polar reaction medium. However, such phase separation is not as convenient as with solid phase synthesis where simple filtration is used to isolate the solid-bound species. Moreover, the IL-bound species usually phase-separates from the solution phase as a viscous liquid, making further purification difficult. A further problem commonly observed with IL-supported synthesis is that the phase tag role played by the IL moiety is reduced when large oligomers are bound to the ionic liquid support. As is commonly observed with most soluble phase tags, the binding of large oligomers adversely affects the characteristic properties (e.g. solubility) of the ionic liquid.

The present specification refers to a number of documents, the contents of which are herein incorporated by reference in their entirety.

SUMMARY OF THE INVENTION

The present disclosure relates to imidazolium-type ionic oligomers.

In an embodiment, the present disclosure relates to structurally defined imidazolium-type ionic oligomers as soluble/solid supports for biopolymer synthesis. Typically, such structurally defined imidazolium-type ionic oligomers combine the benefits and advantages common to solution-phase and solid phase syntheses in that the reactions can be conducted in a substantially homogenous phase and the reaction products can be readily isolated by means of a simple purification process.

In an embodiment, the present disclosure relates to structurally defined imidazolium-type ionic oligomers as soluble/solid supports for oligopeptide synthesis.

In an embodiment, the present disclosure relates to structurally defined imidazolium-type ionic oligomers as soluble/solid supports for oligosaccharide synthesis.

In an embodiment, the present disclosure relates to structurally defined imidazolium-type ionic oligomers as soluble/solid supports for oligonucleotide synthesis.

In an embodiment, the present disclosure relates to an imidazolium-type ionic oligomer of general formula:

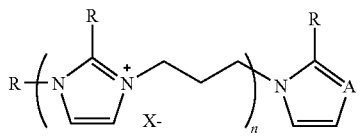

wherein:
n is an integer ranging from 1 to 20;
A is N or

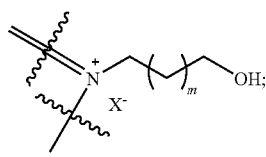

m is an integer ranging from 1 to 5;
X is selected from the group consisting of Br, OTf, $CF_3CO_2$, $CH_3CO_2$, $BF_4$, $PF_6$, $NTf_2$, F, Cl and I; and
R is selected from the group consisting of hydrogen and $C_{1-10}$ alkyl.

In an embodiment, the present disclosure relates to a method for the preparation of structurally defined imidazolium-type ionic oligomers.

In an embodiment, the present disclosure relates to a method for preparing an oligopeptide, the method comprising:
a) contacting a first suitably protected amino acid with an imidazolium-type oligomer of the formula:

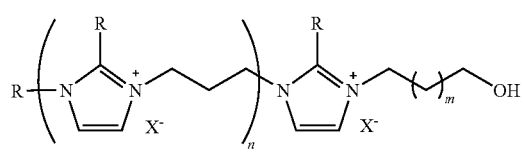

wherein:
n is an integer ranging from 1 to 20;
m is an integer ranging from 1 to 5;
X is selected from the group consisting of Br, OTf, $CF_3CO_2$, $CH_3CO_2$, $BF_4$, $PF_6$, $NTf_2$, F, Cl and I; and
R is selected from the group consisting of hydrogen and $C_{1-10}$ alkyl;
to provide an oligomer bound amino acid; and
b) reacting the oligomer bound amino acid with a second suitably protected amino acid.

In an embodiment, the present disclosure relates to a method for preparing an oligopeptide, the method comprising:
a) contacting a first suitably protected amino acid with an imidazolium-type oligomer of the formula:

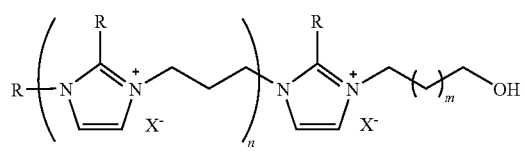

wherein:
n is an integer ranging from 1 to 20;
m is an integer ranging from 1 to 5;
X is selected from the group consisting of Br, OTf, $CF_3CO_2$, $CH_3CO_2$, $BF_4$, $PF_6$, $NTf_2$, F, Cl and I; and
R is selected from the group consisting of hydrogen and $C_{1-10}$ alkyl;
to provide an oligomer bound amino acid;
b) reacting the oligomer bound amino acid with a second suitably protected amino acid; and
c) repeating step b) any number of times to provide an oligomer-bound oligopeptide.

In an embodiment, the present disclosure relates to a method for preparing an oligopeptide, the method comprising:
a) contacting a first suitably protected amino acid with an imidazolium-type oligomer of the formula:

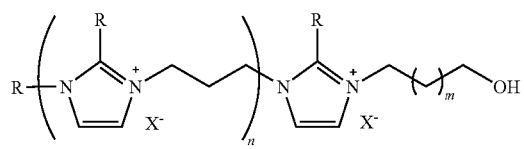

wherein:
n is an integer ranging from 1 to 20;
m is an integer ranging from 1 to 5;
X is selected from the group consisting of Br, OTf, $CF_3CO_2$, $CH_3CO_2$, $BF_4$, $PF_6$, $NTf_2$, F, Cl and I; and
R is selected from the group consisting of hydrogen and $C_{1-10}$ alkyl;
to provide an oligomer bound amino acid;
b) reacting the oligomer bound amino acid with a second suitably protected amino acid;
c) repeating step b) any number of times to provide an oligomer-bound oligopeptide; and
d) isolating the oligopeptide.

In an embodiment, the present disclosure relates to an ionic oligomer-supported process for the synthesis of oligomers, including but not limited to oligopeptides, oligosaccharides and oligonucleotides, wherein the ionic oligomer is a structurally defined imidazolium-type ionic oligomer.

In an embodiment, the present disclosure relates to a novel solution phase method for the synthesis of oligopeptides, the method being supported by imidazolium-type ionic oligomers.

In an embodiment, the present disclosure relates to a novel solution phase method for the synthesis of oligosaccharides, the method being supported by imidazolium-type ionic oligomers.

In an embodiment, the present disclosure relates to a novel solution phase method for the synthesis of oligonucleotides, the method being supported by imidazolium type ionic oligomers.

The foregoing and other advantages and features of the present disclosure will become more apparent upon reading the following non restrictive description of illustrative embodiments thereof, given by way of example only.

DETAILED DESCRIPTION OF ILLUSTRATIVE EMBODIMENTS

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

The term "amino acid", as used herein, is understood as including both the L and D isomers of the naturally occurring amino acids, as well as other non-proteinaceous amino acids used in peptide chemistry to prepare synthetic analogs of peptides. Examples of naturally-occurring amino acids include, but are not limited to glycine, alanine, valine, leucine, isoleucine, serine, and threonine. Examples of non-proteinaceous amino acids include, but are not limited to norleucine, norvaline, cyclohexyl alanine, biphenyl alanine, homophenyl alanine, naphthyl alanine, pyridyl alanine, and substituted phenyl alanines (substituted with one or more substituents including but not limited to alkoxy, halogen and nitro groups). Beta and gamma amino acids are also within the scope of the term "amino acid". Amino acids protected by standard protecting groups commonly used in peptide synthesis are also within the scope of the term "amino acid". These compounds are known to persons skilled in the art of peptide chemistry. Commonly used amino acid protecting groups are disclosed in Greene, "Protective Groups In Organic Synthesis, $3^{rd}$ Edition" (John Wiley & Sons, New York, 1999), which is incorporated herein by reference.

The term "nucleotide", as used herein, is understood as referring to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. The term "nucleotide" is also used herein to encompass "modified nucleotides" which comprise at least one modification selected from (a) an alternative linking group, (b) an analogous form of purine, (c) an analogous form of pyrimidine, or (d) an analogous sugar. Nucleotides protected by standard protecting groups commonly used in oligonucleotide synthesis are also within the scope of the term "nucleotide". These compounds are known to persons skilled in the art of nucleotide chemistry.

The term "saccharide", as used herein, is understood as referring to a carbohydrate which is a polyhydroxy aldehyde or ketone, or derivative thereof, having the empirical formula $(CH_2O)_n$ wherein n is a whole integer, typically greater than 3. Monosaccharides, or simple sugars, consist of a single polyhydroxy aldehyde or ketone unit. Monosaccharides include, but are not limited to, ribose, 2-deoxy-ribose, glucose, mannose, xylose, galactose, fucose, fructose, etc. Disaccharides contain two monosaccharide units joined by a glycosidic linkage. Disaccharides include, for example, sucrose, lactose, maltose, cellobiose, and the like. Oligosaccharides typically contain from 2 to 10 monosaccharide units joined in glycosidic linkage. Polysaccharides (glycans) typically contain more than 10 such units and include, but are not limited to, molecules such as heparin, heparan sulfate, chondroitin sulfate, dermatan sulfate and polysaccharide derivatives thereof. The term "sugar" generally refers to mono-, di- or oligosaccharides. A saccharide may be substituted, for example, glucosamine, galactosamine, acetylglucose, acetylgalactose, N-acetylglucosamine, N-acetyl-galactosamine, galactosyl-N-acetylglucosamine, N-acetylneuraminic acid (sialic acid), etc. A saccharide may also reside as a component part of a larger molecule, for example, as the saccharide moiety of a nucleoside, a nucleotide, a polynucleotide, a DNA, an RNA, etc. The term "saccharide", as used herein, is also understood as encompassing modified saccharides such as those comprising at least one modification selected from (a) replacement of one or more of the OH groups by substituents including but not limited to H, $NH_2$, halogen, alkyl, aryl; (b) oxidation of one or more of the OH groups into functional groups including aldehydes, ketones, acids, esters, and derivatives thereof. Saccharides protected by standard protecting groups commonly used in oligosaccharide synthesis are also within the scope of the term "saccharide". These compounds are known to persons skilled in the art of saccharide chemistry.

The terms "growing oligopeptide chain", "growing oligosaccharide chain" and "growing oligonucleotide chain", as used herein, refers to a chain that has been prepared by the sequential addition of amino acids, saccharides or nucleotides, optionally suitably protected. After each reaction cycle the growing oligopeptide, oligosaccharide or oligonucleotide increases in length by at least one amino acid, saccharide or nucleotide, and becomes the starting material for the next reaction cycle. As used herein, this term can refer to either starting material or product and one of ordinary skill in the art will recognize what is intended by the term in a particular context.

The term "alkyl group", as used herein, is understood as referring to a saturated, monovalent unbranched or branched hydrocarbon chain. Examples of alkyl groups include, but are not limited to, $C_{1-10}$ alkyl groups. Examples of $C_{1-10}$ alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, nonyl and decyl.

The term "aryl", as used herein, is understood as referring to 5-, 6- and 7-membered aromatic groups that may include from zero to four heteroatoms in the ring, for example, phenyl, pyrrolyl, furyl, thiophenyl, imidazolyl, oxazole, thiazolyl, triazolyl, pyrazolyl, pyridyl, pyrazinyl, pyridazinyl and pyrimidinyl, and the like. Those aryl groups having heteroatoms in the ring structure may also be referred to as "aryl heterocycles" or "heteroaromatics". The aromatic ring can be substituted at one or more ring positions. Aryl groups can also be part of a polycyclic group. For example, aryl groups include fused aromatic moieties such as naphthyl, anthracenyl, quinolyl, indolyl, and the like.

The term "halogen", as used herein, is understood as referring to fluorine, chlorine, bromine, or iodine. Correspondingly, the meaning of the term "halo" is understood to encompass fluoro, chloro, bromo, and iodo.

Protecting groups in the present disclosure are used in conjunction with biopolymer syntheses. The protecting groups block a reactive end of the monomer (i.e. amino acid, saccharide or nucleotide), oligopeptide, oligosaccharide or oligonucleotide. The nature of the chemical synthesis will dictate which reactive group will require a protecting group. Regardless of the specific use, protecting groups are employed to protect a moiety on a molecule from reacting with another reagent. Protecting groups as used in the present disclosure have the following characteristics: they prevent selected reagents from modifying the group to which they are attached; they are stable (that is, they remain attached to the molecule) to the synthesis reaction conditions; and they are removable under conditions that do not adversely affect the remaining structure. The selection of a suitable protecting group will depend, of course, on the chemical nature of the monomer unit and/or oligomer, as well as the specific reagents they are to protect against. It is well within the capacity of a skilled technician to select a suitable protecting group for a given reaction sequence.

The present description refers to a number of chemical terms and abbreviations used by those skilled in the art. Nevertheless, definitions of selected terms are provided for clarity and consistency.

Abbreviations: Boc: tert-Butoxycabonyl; TFA: Trifluoroacetic acid; HBTU: O-(Benzotriazol-1-yl)-N,N,N',N'-tetramethyluronium hexa-fluorophosphate; HOBT: 1-Hydroxybenzotriazole; DIPEA: N,N-Diisopropylethylamine; DMAP: 4-Dimethylaminopyridine; DCC: 1,3-Dicyclohexylcarbodiimide; Bzl: Benzyl; TLC: Thin Layer Chromatography; NMR: Nuclear Magnetic Resonance; MS: Mass Spectroscopy; ESI: Electrospray Ionization; FAB: Fast Atom Bombardment; PEG: Polyethylene Glycol; SPE: Solid-Phase Extraction; IL: Ionic Liquid; ILSS: Ionic Liquid Supported Synthesis; TGA: Thermogravimetric Analysis; RP: Residue Percentage; ODT: Onset Decomposing Temperatures; DMF: Dimethylformamide; DMSO: Dimethyl Sulfoxide; THF: Tetrahydrofuran.

The present specification relates to structurally defined imidazolium-type ionic oligomers. The preparation of such structurally defined imidazolium-type ionic oligomers, starting from commercially available 1,2-dimethylimidazole (1), via either one of two routes (c to g versus h to l), is illustrated herein below in Scheme 1. Additional treatment of either compound 8 or 13 with 1,3-dibromopropane, followed by 2-methylimidazole, can further extend the imidazolium oligomer chain. Each of the steps in the synthesis takes place in good yield with ease of purification by phase separation, resulting in good overall yields in multi-gram quantities. A distinguishing feature between the two synthetic routes is that the products comprise different anions. The presence of different anions imparts distinct solubility characteristic on the product and thus entails distinct purification procedures. For example, when compound 3 was treated with 1,3-dibromopropane in $CH_3CN$ under refluxing conditions, compound 9 precipitated out of the reaction mixture due to its low solubility in $CH_3CN$. Compound 9 was obtained as a solid material in near quantitative yield (98%) having a melting point of 201° C. However, compound 5, having a boiling point of 76° C., proved to be soluble in $CH_3CN$.

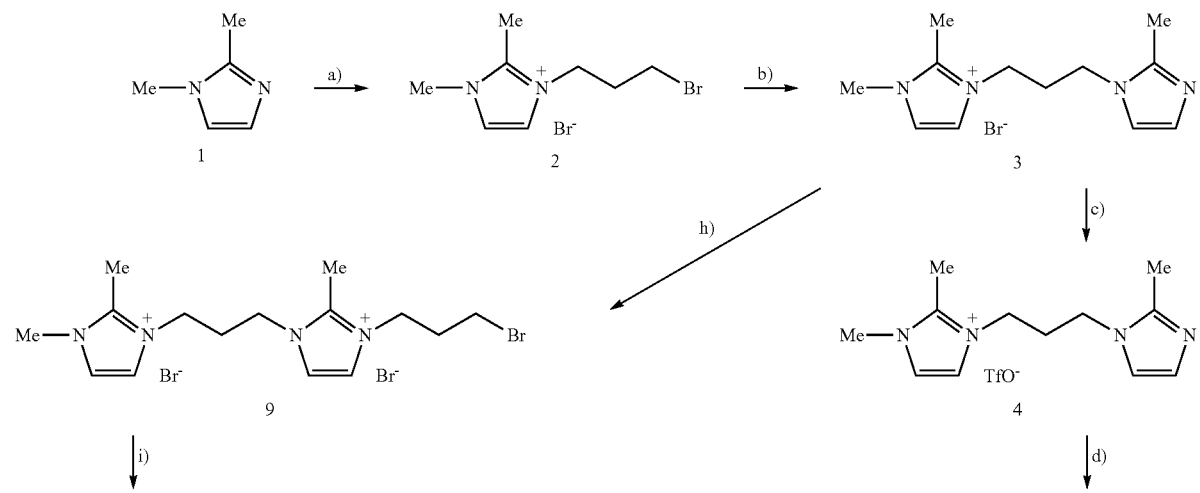

Scheme 1

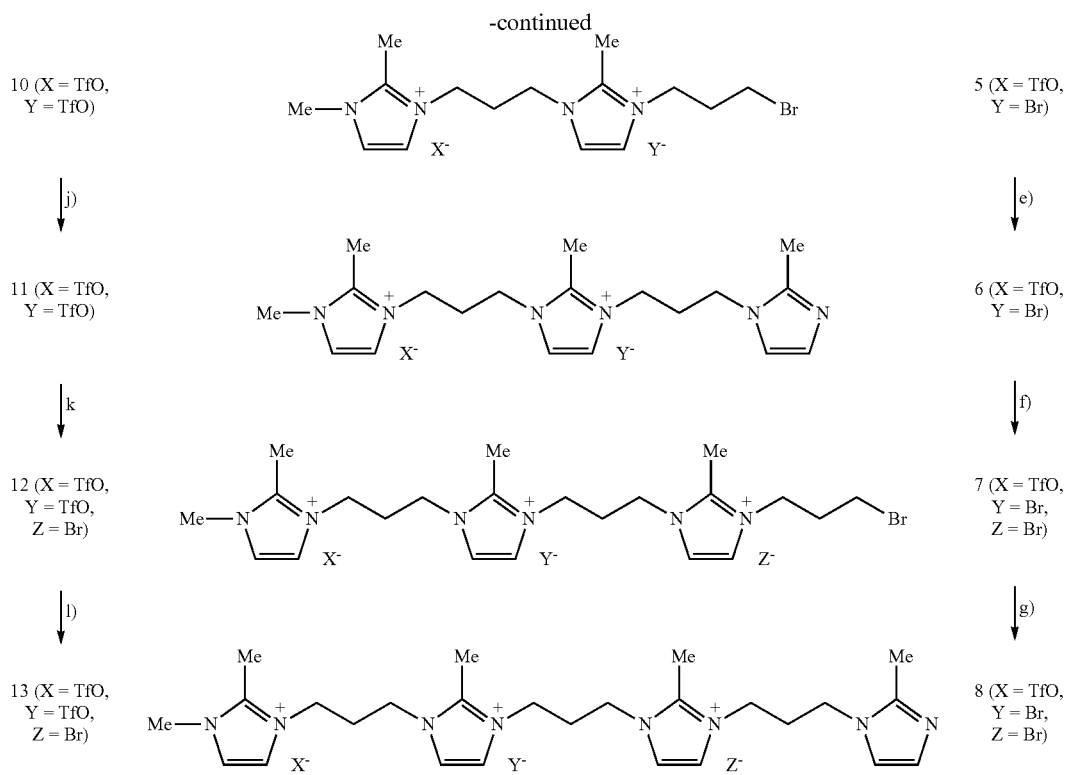

a) 1,3-dibromopropane (2 equiv.), CH₃CN, reflux, 14 h, 80%;
b) 2-methylimidazole, (2 equiv.), CH₃CN, reflux, 24 h, then K₂CO₃, H₂O, rt, 1 h, 74%;
c) AgOTf (1 equiv.), CH₃CN, rt, 1 h, 100%;
d) 1,3-dibromopropane (20 equiv.), CH₃CN, reflux, 17 h, 80%;
e) 2-methylimidazole (3.6 equiv.), CH₃CN, reflux, 24 h, then K₂CO₃, H₂O, rt, 1 h, 74%;
f) 1,3-dibromopropane (20 equiv.), CH₃CN, reflux, 26 h, 84%;
g) 2-methylimidazole (3.4 equiv.), CH₃CN, reflux, 24 h, then K₂CO₃, H₂O, rt 1 h, 75%;
h) 1,3-dibromopropane (10 equiv.), CH₃CN, reflux, 25 h, 98%;
i) AgOTf (1 equiv.), CH₃CN/CH₃OH (v/v = 3:1), rt, 1 h, 100%;
j) 2-methylimidazole (3.2 equiv.), CH₃CN, reflux, 24 h, then K₂CO₃, H₂O, rt, 30 min, 85%;
k) 1,3-dibromopropane (20 equiv.), CH₃CN, reflux, 28 h, 80%;
l) 2-methylimidazole (4 equiv.), CH₃CN, reflux, 24 h, then K₂CO₃, H₂O, rt, 30 min, 70%.

The thermal stability of the imidazolium-type ionic oligomers was measured by thermogravimetric analysis (TGA).[42] The onset decomposing temperatures (ODTs) and residue percentages (RPs) are summarized hereinbelow in Table 1. The observed results are indicative of the imidazolium-type ionic oligomers having good thermal stability with onset decomposing temperatures exceeding 212° C. The imidazolium-type ionic oligomers were observed to be more stable than the non-ionic liquid starting material 1,2-dimethylimidazole (1) (entry 1). Some of the imidazolium-type ionic oligomers were even observed to be more stable than conventional types of ILs (entries 14 and 15).

TABLE 1

Onset decomposing temperatures (ODTs) and residue percentages (RPs) as observed by thermogravimetric analysis (TGA).

| Entry | Sample | ODT (° C.) | RP (%) |
|---|---|---|---|
| 1 | 1 | 80.6 | 0.18 |
| 2 | 3 | 287.8 | 1.53 |
| 3 | 4 | 293.9 | 1.71 |
| 4 | 6 | 329.6 | 1.38 |
| 5 | 11 | 326.2 | 1.76 |
| 6 | 8 | 351.6 | 0.59 |
| 7 | 13 | 336.4 | 0.58 |
| 8 | 2 | 215.8 | 0.10 |
| 9 | 5 | 239.4 | 0.59 |
| 10 | 9 | 212.2 | 1.89 |
| 11 | 10 | 277.8 | 0.50 |
| 12 | 7 | 252.3 | 0.17 |
| 13 | 12 | 318.9 | 2.10 |
| 14 | 14 | 291.8 | 0.50 |
| 15 | 20 | 317.0 | 0.17 |
| 16 | 16 | 296.5 | 0.19 |
| 17 | 17 | 310.4 | 1.40 |
| 18 | 19 | 337.9 | 2.21 |

It can be concluded that there exits a direct link between the number of charges and the onset decomposing temperature. Typically, compounds having a larger number of charges will exhibit higher onset decomposing temperatures. This conclusion is supported by comparing the observed onset decomposing temperatures of compounds 4, 6 and 8 respectively (entries 3, 4 and 6). The onset decomposing temperature increases from 293.9° C. to 329.6° C. to 351.6° C., with increasing imidazolium units. A similar trend can be observed by comparing the onset decomposing temperature of compounds 2, 5 and 7 (entries 8, 9 and 12), as well as compounds 4, 11 and 13 respectively (entries 3, 5 and 7).

Anion exchange from bromide to triflate was observed to increase the thermal stability of the imidazolium-type ionic oligomers. This conclusion is supported by comparing the observed onset decomposing temperatures of compounds 5, 9 and 10 respectively (entries 9, 10 and 11). These compounds possess identical cationic structures, but differ in the nature of their anionic counterions. The onset decomposing temperatures were observed to decrease in going from compound 10 (comprising two triflate anions) to compound 5 (comprising one triflate and one bromide anion) to compound 9 (comprising two bromide anions). A similar trend can be observed by comparing the onset decomposing temperature of compounds 7 and 12 (entries 12 and 13) as well as compounds 3 and 4 respectively (entries 2 and 3).

The low residue percentages, ranging from about 0.10% to about 2.20%, are indicative of the imidazolium-type ionic oligomers comprising only traces of inorganic salt impurities. The inorganic salts are efficiently removed during the purification procedures.

Solubility tests indicate that compounds comprising multiple imidazolium units are typically more soluble in polar protic solvents such as water and alcohols as well as in polar aprotic solvents such a DMF, DMSO, $CH_3CN$ and $CH_3NO_2$. However, such compounds are typically less soluble in $CH_2Cl_2$ and ethyl acetate, and insoluble in THF, $Et_2O$, $CHCl_3$ and alkanes. However, the solubility of the imidazolium-type ionic oligomers can be tuned by anion exchange. Comparing imidazolium-type ionic oligomers of identical cationic structure, oligomers comprising bromine anions were observed to be less soluble in $CH_3CN$ while exhibiting a higher affinity for moisture than those comprising triflate anions. This observation is particularly evident with imidazolium-type ionic oligomers comprising at least two or three bromide ions. Comparing the solubility of compounds 5, 9 and 10 respectively, it was observed that compound 9 was insoluble in $CH_3CN$, while compounds 5 and 10 were soluble in therein. Moreover, compounds 7 and 8, each comprising a pair of bromide ions and a triflate ion, were observed to be less soluble in $CH_3CN$ than compounds 12 and 13, each comprising a pair of triflate ions and a bromide ion.

The number of imidazolium units in a compound was observed to have an impact on the moisture affinity of the compound. Typically, compounds having a larger number of imidazolium units will exhibit reduced moisture affinity. For example, compounds 3 and 4 absorb moisture from the atmosphere at a significantly slower rate than compound 2. Moreover, compounds 6, 8, 11 and 13 did substantially not absorb moisture from the atmosphere.

In an embodiment, the present disclosure relates to a novel solution phase method for the synthesis of oligopeptides, the method being supported by imidazolium-type ionic oligomers. Thus far, the automated solid-phase synthesis (SPS) using polymer resins or glass beads as solid supports, remains the most popular strategy in peptide synthesis. However, in addition to the previously mentioned drawbacks, the linear assembly of amino acids in SPS, necessitated by the inefficiency of block coupling, leads to long synthetic routes for peptide assembly.

In accordance with the present disclosure, the preparation of further non-limiting examples of structurally defined imidazolium-type ionic liquids 20-23, is illustrated hereinbelow in Scheme 2. The imidazolium-type ionic liquids 20-23 were subsequently used as IL-supports for oligopeptide synthesis. In the case of compound 21, a hydroxyhexyl linker was used as opposed to a hydroxypropyl linker as in compounds 20, 22 and 23. When the imidazolium dimer 3 was treated with 3-bromopropanol under conditions similar to the other cases illustrated in Scheme 2, compound 9 was unexpectedly obtained instead of the expected compound 15. This can be explained by the low solubility of compound 9 in $CH_3CN$, causing it to precipitate out from the reaction mixture, driving the reaction to generate additional compound 9. However, this problem was overcome by the use of imidazolium dimer 4 (the corresponding triflate salt of 3) as the starting material, compound 4 having improved solubility in $CH_3CN$. The thermal stability of the imidazolium salts 14, 16, 17, 19 and 20 was also measured by thermogravimetric analysis (Table 1, entries 14-18), suggesting good thermal stability.

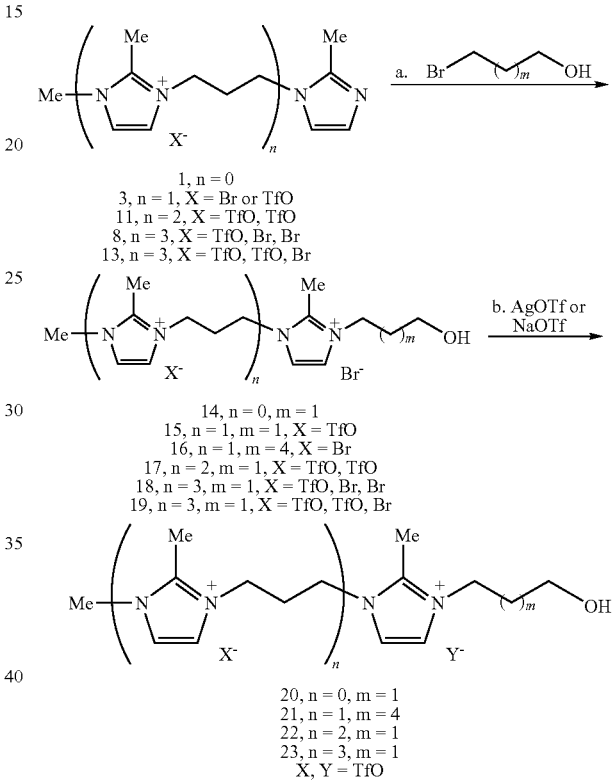

Scheme 2

A typical imidazolium oligomer IL-supported synthesis of a peptide, in accordance with the present disclosure, is illustrated hereinbelow in Scheme 3. The synthesized peptide sequence represents a segment of the natural peptide Mucin4 (MUC4)[43] and is mostly composed of serine and threonine amino acid units, both of which play a significant role in binding glycals in glycoproteins.[44] The first amino acid was covalently bound to either of the imidazolium IL-supports 20-23 through an esterification reaction using 1,3-dicyclohexylcarbodimide (DCC) as the coupling reagent and 4-dimethylaminopyridine (DMAP) as the catalyst in $CH_3CN$ at room temperature. The white precipitate (i.e. dicyclohexylurea) was filtered off and excess reagents and other by-products were removed by washing with either $Et_2O$ or a solvent mixture composed of $Et_2O$ and EtOAc (v/v=1:1). The imidazolium dimer (21) and imidazolium oligomer (22 or 23)-supported products were obtained as solid materials, whereas the imidazolium monomer (20)-supported product was obtained as a thick oil.

The acid-labile Boc-protecting group of the imidazolium supported amino acids was removed by treatment with trifluoroacetic acid (TFA) in $CH_2Cl_2$ and washed away with $Et_2O$, Subsequent amino acid coupling was achieved using a combination of HBTU and HOBT in the presence of Hünig's base (DIPEA), which acts as an acid scavenger, substantially preventing protonation of the amine functionality of the coupled amino acid. This generic coupling protocol was slightly modified from previously reported procedures in which PyBOP was used as the coupling reagent. The pyrrolidine side-product which is generated when using PyBOP, is difficult to remove from the reaction product during purification.[15e]

The imidazolium dimer (21) or imidazolium oligomer (22 or 23)-supported amino products were purified using simple procedures. Upon completion of the reaction, the reaction mixture was concentrated under reduced pressure, followed by the subsequent addition of $Et_2O$ to precipitate the crude product. The liquid phase can be removed by decantation or other means within the capacity of a skilled technician. The solid phase was washed with water and $Et_2O$, yielding a powder following drying. The imidazolium monomer (20)-supported amino acid product was obtained as viscous oily layer upon the addition of $Et_2O$ to the concentrated reaction mixture. Repeated stirring of the oily product layer was necessary to allow any by-products and excess reagents to be removed by solvent washing. The purification process involving the imidazolium monomer (20)-supported amino acid product becomes more difficult with larger-scale reactions. Contrary to solid phase synthesis, the imidazolium support-bound products can be readily characterized using common methods such as solution NMR and MS.

The nonapeptide product 25 was readily obtained in good overall yield. Cleavage of the peptide products form the imidazolium support is achieved through hydrolysis of the ester linkage under aqueous basic conditions. In an embodiment, the imidazolium support-bound products were hydrolyzed using an aqueous solution of LiOH or NaOH, followed by the addition of THF or $CH_3CN$ to yield the corresponding peptide products. Other hydrolysis conditions are known in the art, and are within the capacity of a skilled technician.

Further purification of the peptide products following cleavage from the imidazolium support was achieved by means of washing with water. Chromatographic purification was not required in view of the aqueous solubility of the imidazolium supports. The protected peptide products are insoluble in water. The imidazolium supports can subsequently be recovered from the aqueous phase by techniques well within the capacity of a skilled technician. The peptide products obtained had a purity ranging from about 85-95% as confirmed by NMR, MS and HPLC analysis.[45] It is of interest to note that the purity of the peptide products obtained by means of the imidazolium supports of the present disclosure, exceeds that obtained using solid phase synthesis. The purity of the peptide products obtained by means of the imidazolium supports as described herein exceeds that achieved by means of solid phase synthesis. Solid phase synthesis typically provides protected peptides having a purity ranging from 70-80% following cleavage from the supports.

The chemical assembly of the oligopepticles as illustrated in Scheme 3 was conducted in a substantially homogeneous solution phase, without the need for a large excess of reagents. Typically, 2-2.5 equivalents of amino acid relative to imidazolium support or imidazolium supported product were used. Surprisingly, it was observed that peptide block coupling could be achieved using the imidazolium IL supports of the present disclosure. [6+6] and [9+6] block coupling using the imidazolium IL supports of the present disclosure is illustrated hereinbelow in Scheme 3. The protected hexapeptide 27, obtained by cleavage from the supported precursor 26, was coupled to 26 using the generic coupling protocol described hereinabove to provide the [6+6] adduct 28 in 95% yield. Similarly, protected hexapeptide 27 was coupled to imidazolium supported nonapeptide 25 to provide the [9+6] adduct 29 in 99% yield. The peptide products were isolated and purified using the standard protocol as described hereinabove.

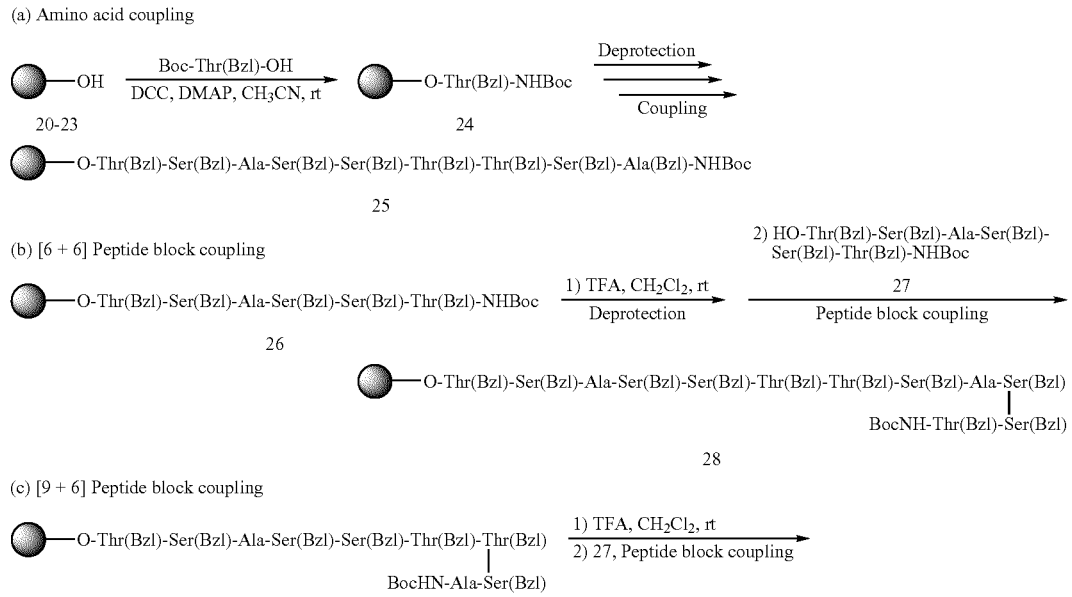

Scheme 3

-continued

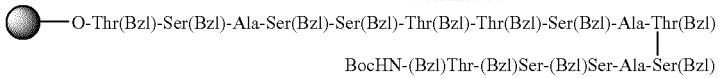
O-Thr(Bzl)-Ser(Bzl)-Ala-Ser(Bzl)-Ser(Bzl)-Thr(Bzl)-Thr(Bzl)-Ser(Bzl)-Ala-Thr(Bzl)
|
BocHN-(Bzl)Thr-(Bzl)Ser-(Bzl)Ser-Ala-Ser(Bzl)

29

For linker anchoring: Amino acid (2 equiv.), DCC (2 equiv.), DMAP (0.2 equiv.), $CH_3CN$, rt, 16 h 83-92%;
For Boc deprotection: TFA (40-60 equiv. or 5-10% in $CH_2Cl_2$), 1 h, 100%;
For amino acid and peptide block coupling: Amino acid or hexa-amino-acid peptide (2.5 equiv.), HBTU (2.5 equiv.),
HOBT (2.5 equiv.), DIPEA (5 equiv.), $CH_3CN$, rt, 24 h-31 h, 95-100%.

The present invention is illustrated in further detail by the following non-restrictive description of illustrative embodiments.

Experimental

General: All reagents were commercially obtained from Aldrich Chemical Co. and were used without further purification unless otherwise noted. Solvents were of reagent grade and, if necessary, were dried by standard procedures. $^1$H NMR, $^{13}$C NMR and COSY NMR spectra were acquired using Varian Mercury 300 MHz, 400 MHz and Unity 500 MHz spectrometers respectively, equipped with Sun workstations. The proton chemical shifts were reported in parts per million on the δ scale, referenced to the residual proton resonance in $CDCl_3$ (δ 7.24 ppm) or $D_2O$ (δ 4.67 ppm). The carbon chemical shifts were reported in parts per million on the δ scale, internally referenced to the solvent resonance in $CDCl_3$ (δ 77.0 ppm). The proton and carbon assignments were made by standard gCOSY experiments. Melting points were taken using a standard melting point apparatus without correcting the thermometer. High resolution mass spectrometric analyses were performed on a VG Micromass ZAB 2F HS (FAB) or a Microm as Quattro II triple quadrupole mass spectrometer (Manchester, UK) equipped with an electrospray ionization source (ESI). Typically only the ion corresponding to the cation (C) component was analyzed. Thermogravimetric analysis (TGA) measurements were performed on a TGA Q500 from TA instruments. The running method used was ramped from 25° C. to 550° C., 20° C./min, under nitrogen, switching to air and then ramped at 20° C./min to 700° C. The type of pan used was platinum. High-pressure liquid chromatography (HPLC) analyses were performed using a reverse phase $C_{18}$ column (Agilent Zorbax Extend-C18). The elution was performed using a linear gradient from 50% to 100% of B in A over 20 min, followed by a linear gradient elution from 100% to 50% of B in A over 10 min, where A is $H_2O$/0.05% TFA (v/v) and B is $CH_3CN$/0.05% TFA (v/v), at a flow rate of 0.8 mL/min. The eluted compounds were detected by UV absorbance at 210 nm.

PREPARATION OF IMIDAZOLIUM SALT OLIGOMERS

Example 1

Preparation of Compound 2

To a solution of 1,3-dibromopropane (12.5 mL, 122.4 mmol) in acetonitrile (25 mL) was added dropwise, at 90° C., a solution of 1,2-dimethylimidazole (1) (5.66 g, 59.0 mmol) in acetonitrile (10 mL). After refluxing at 90° C. for 14 hours, the solvent was removed by rotary evaporation under reduced pressure and the residue washed several times with diethyl ether. Following drying in vacuo, a white powder was obtained which was subsequently added to dry acetonitrile (40 mL). The insoluble precipitate was removed by means of phase separation following centrifugation. The solution phase was collected and the solvent removed by rotary evaporation under reduced pressure. The resulting product was dried in vacuo to yield a white solid (14.2 g; m.p.: 96-98° C.; Yield: 80%). $^1$H NMR (400 MHz, $D_2O$): δ 7.30 (d, 1H, J=2 Hz), 7.24 (d, 1H, J=2 Hz), 4.20 (t, 2H, J=7.2 Hz), 3.67 (s, 3H), 3.37 (t, 2H, J=5.6 Hz), 2.53 (s, 3H), 2.28 (m, 2H); $^{13}$C NMR (400 MHz, $D_2O$): δ 144.72, 122.67, 121.00, 46.70, 35.29, 31.98, 30.26, 9.81; HRMS (ESI): calculated for $C_8H_{14}N_2Br$ ($C^+$) 217.0337; found: 217.0334.

Example 2

Preparation of Compound 3

To a flask comprising compound 2 (22.05 g, 74.0 mmol) and 2-methylimidazole (13.53 g, 164.9 mmol), was added dry acetonitrile (200 mL) under a nitrogen atmosphere. The reaction mixture was refluxed for 24 hours and then cooled to room temperature. The solvent was removed by rotary evaporation under reduced pressure and the residue washed several times with diethyl ether and THF to yield a white powder. The phase separation during the washing process was achieved by means of centrifugation and decantation. Following drying in vacuo over a period of two hours, the white powder was added to an aqueous $K_2CO_3$ solution (150 mL; pH 11) and stirred over a period of 30 minutes. The water was subsequently removed by means of freeze-drying and the residue added to acetonitrile. The insoluble inorganic salt was removed by means of filtration and the filtrate collected and rotary evaporated under reduced pressure to dryness. The residue was washed with THF and ether to yield a white powder (16.4 g; m.p.: 159-161° C.; Yield: 74%). $^1$H NMR (400 MHz, $D_2O$): δ 7.12-7.10 (m, 2H), 6.85 (d, 1H, J=1.2 Hz), 6.68 (d, 1H, J=1.2 Hz), 3.95 (t, 2H, J=7.2 Hz), 3.86 (t, 2H, 6.8 Hz), 3.55 (s, 3H), 2.32 (s, 3H), 2.14 (m, 5H); $^{13}$C NMR (400 MHz, $D_2O$): δ 145.99, 144.40, 126.06, 122.60, 120.51, 120.20, 45.62, 43.08, 35.02, 29.70, 12.09, 9.29; HRMS (ESI): calculated for $C_{12}H_{19}N_4$ ($C^f$) 219.1604; found: 219.1604.

Example 3

Preparation of Compound 4

To a solution of compound 3 (4.88 g, 16.3 mmol) in acetonitrile (60 mL), was added a solution of AgOTf (4.18 g, 16.32 mmol) in acetonitrile (10 mL). The resulting mixture was stirred in the dark over a period of 1 hour and filtered to remove the yellow precipitate. The filtrate was rotary evaporated under reduced pressure to yield a white solid (6.06 g; m.p.: 120-122° C.; Yield: 100%). $^1$H NMR (400 MHz, $D_2O$): δ 7.13 (m, 2H), 6.87 (d, 1H, J=1.2 Hz), 6.71 (d, 1H, J=1.2 Hz), 3.96 (t, 2H, 7.2 Hz), 3.87 (t, 2H, 7.2 Hz), 3.56 (s, 3H), 2.33 (s, 3H), 2.14 (m, 5H); $^{13}$C NMR (400 MHz, $D_2O$): δ145.97, 144.42, 125.80, 122.57, 120.45, 120.15, 45.34, 42.84, 34.66, 29.40, 11.63, 8.78; HRMS (ESI): calculated for $C_{12}H_{19}N_4$ ($C^+$) 219.1604; found: 219.1604.

Example 4

Preparation of Compound 5

To a flask comprising compound 4 (5.51 g, 15.0 mmol), was added 1,3-dibromopropane (30 mL, 293.7 mmol) and dry acetonitrile (100 mL). The reaction mixture was refluxed for 17 hours under a nitrogen atmosphere and then cooled to room temperature. The solvent was removed by rotary evaporation under reduced pressure and the residue washed several times with diethyl ether. Following drying in vacuo over a period of 30 minutes, a white solid was obtained which was subsequently added to dry acetonitrile (100 mL). The insoluble precipitate was removed by means of phase separation through centrifugation and decantation. The solution phase was collected and the solvent removed by rotary evaporation under reduced pressure. The resulting product was dried in vacuo to yield a fine solid (6.81 g; m.p.: 76-78° C.; Yield: 80%). $^1$H NMR (400 MHz, D$_2$O): δ 7.28 (d, 1H, J=2.4 Hz), 7.24 (d, 1H, J=2.0 Hz), 7.19 (d, 1H, J=2.0 Hz), 7.16 (d, 1H, J=2.4 Hz), 4.13 (t, 2H, J=6.8 Hz), 4.06 (t, 2H, J=7.6 Hz), 3.58 (s, 3H), 3.29 (t, 2H, J=5.6 Hz), 2.48 (s, 3H), 2.41 (s, 3H), 2.20 (m, 4H); $^{13}$C NMR (400 MHz, D$_2$O): δ 144.58, 144.42, 122.67, 121.65, 121.09, 120.43, 46.66, 45.16, 45.10, 34.95, 31.56, 29.70, 29.20, 9.44, 9.21; HRMS (ESI): calculated for C$_{16}$H$_{25}$N$_4$BrO$_3$F$_3$S (M$^+$-Br) 489.0780; found: 489.0777.

Example 5

Preparation of Compound 6

To a flask comprising compound 5 (4.89 g, 8.58 mmol) and 2-methylimidazole (2.56 g, 31.2 mmol), was added dry acetonitrile (45 mL) under a nitrogen atmosphere. The reaction mixture was refluxed for 24 hours at 90° C. and then cooled to room temperature. The solvent was removed by rotary evaporation under reduced pressure and the residue washed several times with diethyl ether and THF. Following drying in vacuo over a period of 30 minutes, a white powder was obtained. The white powder was added to an aqueous K$_2$CO$_3$ solution (60 mL; pH 11) and stirred over a period of 30 minutes. The water was subsequently removed by means of freeze-drying and the residue added to acetonitrile. The insoluble inorganic salt was removed by means of filtration and the filtrate collected and rotary evaporated under reduced pressure to dryness. The residue was washed with THF and ether to yield a white powder (3.59 g; m.p.: 121-123° C.; Yield: 74%). $^1$H NMR (400 MHz, D$_2$O): δ 7.27 (m, 4H), 6.92 (s, 1H), 6.74 (s, 1H), 4.14-4.02 (m, 6H), 3.95 (t, 2H, J=6.4 Hz), 3.65 (s, 3H), 2.48 (s, 3H), 2.43 (s, 3H), 2.21 (m, 7H); $^{13}$C NMR (400 MHz, D$_2$O): δ 146.03, 144.68, 144.22, 126.01, 122.77, 121.32, 121.23, 120.52, 120.17, 45.84, 45.23, 45.18, 43.18, 35.04, 29.47, 29.27, 12.02, 9.34; HRMS (ESI): calculated for C$_{20}$H$_{30}$N$_6$O$_3$F$_3$S (M$^+$-Br) 491.2049; found: 491.2046.

Example 6

Preparation of Compound 7

To a flask comprising compound 6 (3.22 g, 5.65 mmol), was added 1,3-dibromopropane (11 mL, 107.7 mmol) and dry acetonitrile (35 mL). The reaction mixture was refluxed for 26 hours at 90° C. under a nitrogen atmosphere and then cooled to room temperature. The solvent was removed by rotary evaporation under reduced pressure and the residue washed several times with THF and diethyl ether. Following drying in vacuo over a period of 30 minutes, a white solid was obtained which was subsequently added to dry acetonitrile (100 mL). The insoluble precipitate was removed by means of phase separation through centrifugation and decantation. The solution phase was collected and the solvent removed by rotary evaporation under reduced pressure to yield the product as a thick oil (3.66 g; Yield: 84%). $^1$H NMR (400 MHz, D$_2$O): δ 7.31-7.27 (m, 4H), 7.21 (d, 1H, J=2 Hz), 7.18 (d, 1H, J=2 Hz), 4.15 (t, 2H, J=6.8 Hz), 4.11-4.05 (m, 8H), 3.60 (s, 3H), 3.30 (t, 2H, J=6.4 Hz), 2.50 (s, 3H), 2.46 (s, 3H), 2.42 (s, 3H), 2.21 (m, 6H); $^{13}$C NMR (400 MHz, D$_2$O): δ 144.71, 144.56, 122.78, 121.78, 121.30, 121.24, 120.56, 46.58, 45.13, 45.07, 44.99, 34.84, 31.47, 29.71, 29.06, 29.01, 9.28, 9.20, 9.04; HRMS (ESI): calculated for C$_{23}$H$_{36}$N$_6$O$_3$F$_3$SBr (M$^{2+}$-2Br) 306.0847; found: 306.0850.

Example 7

Preparation of Compound 8

To a flask comprising compound 7 (2.42 g, 3.13 mmol) and 2-methylimidazole (0.88 g, 10.7 mmol), was added dry acetonitrile (45 mL) under a nitrogen atmosphere. The reaction mixture was refluxed for 24 hours at 90° C. and then cooled to room temperature. The solvent was removed by rotary evaporation under reduced pressure and the residue washed several times with diethyl ether and THF. Following drying in vacuo over a period of 30 minutes, a white powder was obtained. The white powder was added to an aqueous K$_2$CO$_3$ solution (50 mL; pH 11) and stirred over a period of 30 minutes. The water was subsequently removed by means of freeze-drying and the residue added to acetonitrile. The insoluble inorganic salt was removed by means of filtration and the filtrate collected and rotary evaporated under reduced pressure to dryness. The residue was washed with THF and ether to yield a sticky white foam (1.81 g; Yield: 75%). $^1$H-NMR (400 MHz, D$_2$O): δ 7.30 (m, 2H), 7.25-7.17 (m, 4H), 6.88 (s, 1H), 6.70 (s, 1H), 4.11-4.05 (m, 8H), 4.00 (t, 2H, J=7.2 Hz), 3.91 (t, 2H, J=6.8 Hz), 3.61 (s, 3H), 2.48 (s, 3H), 2.44 (s, 3H), 2.40 (s, 3H), 2.26-2.14 (m, 9H); $^{13}$C NMR (500 MHz, CD$_3$CN): δ 145.17, 145.13, 144.84, 144.55, 127.12, 122.80, 122.56, 121.54, 120.99, 120.01, 119.37, 45.72, 45.18, 42.66, 35.05, 30.32, 29.42, 29.33, 12.38, 9.70, 9.56, 9.49; HRMS (ESI): calculated for C$_{27}$H$_{41}$N$_8$O$_3$F$_3$S (M$^{2+}$-2Br) 307.1481; found: 307.1483.

Example 8

Preparation of Compound 9

To a flask comprising compound 3 (2.75 g, 9.22 mmol), was added 1,3-dibromopropane (10 mL, 97.9 mmol) and dry acetonitrile (100 mL). The reaction mixture was refluxed for 25 hours at 90° C. under a nitrogen atmosphere and then cooled to room temperature. The solvent was removed by rotary evaporation under reduced pressure and the residue washed several times with diethyl ether. Following drying in vacuo, a white powder was obtained (4.52 g; m.p.: 201-203° C.; Yield: 98%). $^1$H NMR (500 MHz, D$_2$O): δ 7.36 (d, 1H, J=2 Hz), 7.33 (d, 1H, J=2 Hz), 7.28 (d, 1H, J=2 Hz), 7.24 (d, 1H, J=2 Hz), 4.19 (t, 2H, J=7 Hz), 4.13 (m, 4H), 3.65 (s, 3H), 3.36 (t, 2H, J=6 Hz), 2.55 (s, 3H), 2.48 (s, 3H), 2.27 (m, 4H); $^{13}$C NMR (400 MHz, D$_2$O): δ 144.71, 144.55, 122.82, 121.87, 121.29, 120.63, 46.87, 45.40, 45.34, 35.23, 31.76, 30.14, 29.38, 9.90, 9.66; HRMS (ESI): calculated for C$_{15}$H$_{25}$N$_4$Br$_2$ (M$^+$-Br) 419.0446; found: 419.0440.

Example 9

Preparation of Compound 10

To a solution of compound 9 (3.19 g, 6.38 mmol) in a mixed solvent system comprising acetonitrile (60 mL) and methanol (18 mL), was added a solution of AgOTf (3.27 g, 12.8 mmol) in acetonitrile (20 mL). The resulting mixture was stirred in the dark over a period of 1 hour and filtered to remove the yellow precipitate. The filtrate was rotary evaporated under reduced pressure to yield a white solid (4.09 g; m.p.: 84-86° C.; Yield: 100%). $^1$H NMR (400 MHz, D$_2$O): δ 7.32 (d, 1H, J=2.4 Hz), 7.28 (d, 1H, J=2.0 Hz), 7.22 (d, 1H, J=2.0 Hz), 4.16 (t, 2H, J=6.8 Hz), 4.08 (m, 4H), 3.1 (s, 3H), 3.22 (d, 2H, J=6 Hz), 2.50 (s, 3H), 2.44 (s, 3H), 2.22 (m, 4H); $^{13}$C NMR (400 MHz, D$_2$O): δ 144.69, 144.52, 122.77, 121.74, 121.18, 120.51, 46.54, 45.03, 44.97, 34.78, 31.43, 29.60, 29.02, 9.17, 8.94; HRMS (ESI): calculated for $C_{16}H_{25}N_4BrO_3F_3S$ (M$^+$-TfO) 489.0780; found: 489.0777.

Example 10

Preparation of Compound 11

To a flask comprising compound 10 (3.87 g, 6.07 mmol) and 2-methylimidazole (1.61 g, 19.7 mmol), was added dry acetonitrile (110 mL) under a nitrogen atmosphere. The reaction mixture was refluxed for 24 hours at 90° C. and then cooled to room temperature. The solvent was removed by rotary evaporation under reduced pressure and the residue washed several times with diethyl ether and THF. Following drying in vacuo over a period of 30 minutes, a white powder was obtained. The white powder was added to an aqueous $K_2CO_3$ solution (50 mL; pH 11) and stirred over a period of 30 minutes. The water was subsequently removed by means of freeze-drying and the residue added to acetonitrile. The insoluble inorganic salt was removed by means of filtration and the filtrate collected and rotary evaporated under reduced pressure to dryness. The residue was washed with THF and ether to yield a white solid (3.27 g; m.p.: 107-109° C.; Yield: 85%). $^1$H NMR (400 MHz, D$_2$O): δ 7.22 (s, 2H), 7.21 (d, 1H, J=2.4 Hz), 7.18 (d, 1H, J=2.4 Hz), 6.87 (d, 1H, J=1.6 Hz), 6.70 (d, 1H, J=1.6 Hz), 4.08-4.01 (m, 4H), 3.99 (t, 2H, J=7.2 Hz), 3.90 (t, 2H, J=6.4 Hz), 3.59 (s, 3H), 2.42 (s, 3H), 2.37 (s, 3H), 2.17 (m, 7H); $^{13}$C NMR (400 MHz, D$_2$O): δ 146.00, 144.69, 144.24, 125.82, 122.75, 121.28, 121.18, 120.46, 120.13, 45.57, 44.97, 44.91, 42.94, 34.75, 29.23, 29.00, 11.64, 8.90; HRMS (ESI): calculated for $C_{20}H_{30}N_6O_3F_3S$ (M$^+$-TfO) 491.2049; found: 491.2046.

Example 11

Preparation of Compound 12

To a flask comprising compound 11 (2.07 g, 3.24 mmol), was added 1,3-dibromopropane (7.0 mL, 68.5 mmol) and dry acetonitrile (45 mL). The reaction mixture was refluxed for 28 hours at 90° C. under a nitrogen atmosphere and then cooled to room temperature. The solvent was removed by rotary evaporation under reduced pressure and the residue washed several times with THF and diethyl ether. Following drying in vacuo over a period of 30 minutes, a white solid was obtained which was subsequently added to dry acetonitrile (80 mL). The insoluble precipitate was removed by means of phase separation through centrifugation and decantation. The solution phase was collected and the solvent removed by rotary evaporation under reduced pressure to yield the product as a white powder (2.19 g; m.p.: 105-107° C.; Yield: 80%). $^1$H-NMR (400 MHz, D$_2$O): δ 7.31 (d, 1H, J=2.4 Hz), 7.28 (m, 2H), 7.27 (d, 1H, J=2.4 Hz), 7.21 (d, 1H, J=2.0 Hz), 7.18 (d, 1H, J=2.0 Hz), 4.15 (t, 2H, J=6.8 Hz), 4.11-4.06 (m, 8H), 3.60 (s, 3H), 3.31 (t, 2H, J=6.4 Hz), 2.50 (s, 3H), 2.47 (s, 3H), 2.43 (s, 3H), 2.22 (m, 6H); $^{13}$C NMR (400 MHz, D$_2$O): δ 144.64, 144.48, 122.73, 121.74, 121.33, 121.16, 120.49, 46.73, 45.26, 45.19, 45.12, 34.97, 31.61, 29.78, 29.23, 29.17, 9.46, 9.35, 9.21; HRMS (ESI): calculated for $C_{24}H_{36}N_6O_6F_6S_2Br$ (M$^+$-Br) 761.1231; found: 761.1219.

Example 12

Preparation of Compound 13

To a flask comprising compound 12 (2.05 g, 2.43 mmol) and 2-methylimidazole (0.80 g, 9.85 mmol), was added dry acetonitrile (45 mL) under a nitrogen atmosphere. The reaction mixture was refluxed for 24 hours at 90° C. and then cooled to room temperature. The solvent was removed by rotary evaporation under reduced pressure and the residue washed several times with diethyl ether and THF. Following drying in vacuo over a period of 30 minutes, a white powder was obtained. The white powder was added to an aqueous $K_2CO_3$ solution (50 mL; pH 11) and stirred over a period of 30 minutes. The water was subsequently removed by means of freeze-drying and the residue added to acetonitrile. The insoluble inorganic salt was removed by means of filtration and the filtrate collected and rotary evaporated under reduced pressure to dryness. The residue was washed with THF and ether to yield a white solid (1.43 g; m.p.: 96-98° C.; Yield: 70%). $^1$H NMR (400 MHz, D$_2$O): δ 7.27 (s, 2H), 7.22 (m, 2H), 7.20 (d, 1H, J=2.4 Hz), 7.19 (d, 1H, J=2.4 Hz), 6.86 (d, 1H, J=1.2 Hz), 6.69 (d, 1H, J=1.2 Hz), 4.07 (m, 8H), 3.98 (t, 2H, 7.6 Hz), 3.89 (t, 2H, J=6.8 Hz), 3.59 (s, 3H), 2.46 (s, 3H), 2.42 (s, 3H), 2.37 (s, 3H), 2.19 (m, 9H); $^{13}$C NMR (400 MHz, D$_2$O) δ 145.95, 144.58, 144.42, 144.14, 126.01, 122.67, 121.29, 121.26, 121.12, 120.43, 120.06, 45.72, 45.19, 45.08, 45.06, 43.04, 34.91, 29.43, 29.18, 29.13, 11.92, 9.30, 9.15; HRMS (ESI): calculated for $C_{28}H_{41}N_8O_6F_6S_2$ (M$^+$-Br) 763.2488; found: 763.2489.

General Procedures for Anchoring Linkers onto Imidazolium Salts

Example 13

Preparation of Compounds 16-19

To a flask comprising an imidazolium salt (1 equiv.) was added bromoalcohol (1.5 equiv.) and dry acetonitrile (10 mL/1 g of imidazolium salt). The reaction mixture was refluxed for 24 hours at 90° C. under a nitrogen atmosphere and then cooled to room temperature. The solvent was removed by rotary evaporation under reduced pressure. The residue was subsequently washed several times with diethyl ether followed by drying in vacuo to yield the product.

Compound 16 was obtained as a white powder (m.p.: 116-118° C.; Yield: 98%). $^1$H NMR (500 MHz, D$_2$O): δ 7.29 (d, 1H, J=2 Hz), 7.28 (d, 1H, J=2 Hz), 7.25 (d, 1H, J=2.5 Hz), 7.22 (d, 1H, J=2.5 Hz), 4.11 (m, 4H), 3.98 (t, 2H, J=7.5 Hz), 3.63 (s, 3H), 3.44 (t, 2H, J=6.5 Hz), 2.48 (s, 3H), 2.46 (s, 3H), 2.24 (m, 2H), 1.69 (m, 2H), 1.39 (m, 2H), 1.21 (m, 4H); $^{13}$C NMR (500 MHz, D$_2$O): δ 144.74, 144.12, 122.80, 121.70, 120.89, 120.56, 61.75, 48.39, 45.08, 45.03, 34.89, 31.18, 29.08, 28.93, 25.42, 24.71, 9.19, 9.12; HRMS (ESI): calculated for $C_{18}H_{32}N_4OBr$ (M$^+$-Br) 399.1754; found: 399.1754.

Compound 17 was obtained as a white powder (m.p.: 90-93° C.; Yield: 87%). $^1$H NMR (400 MHz, D$_2$O): δ 7.30 (m, 2H), 7.28 (d, 1H, J=2 Hz), 7.27 (d, 1H, J=2 Hz), 7.22 (d, 1H, J=2.5 Hz), 7.18 (d, 1H, J=2.5 Hz), 4.07 (m, 10H), 3.60 (s, 3H), 3.46 (t, 2H, J=6 Hz), 2.47 (s, 6H), 2.43 (s, 3H), 2.22 (m, 4H), 1.88 (m, 2H); $^{13}$C NMR (400 MHz, D$_2$O) δ 144.74, 144.58, 144.40, 122.80, 121.74, 121.42, 121.08, 120.59, 58.09, 45.37, 45.18, 45.04, 34.90, 31.26, 29.09, 29.05, 9.32, 9.20, 9.14; HRMS (ESI): calculated for $C_{24}H_{37}N_6O_7F_6S_2$ (M$^+$-Br) 699.2063; found: 699.2067.

Compound 18 was obtained as a white powder (m.p.: 120-122° C.; Yield: 98%). $^1$H NMR (500 MHz, D$_2$O): δ 7.35 (d, 4H), 7.32 (s, 2H), 7.27 (d, 1H, J=1.5 Hz), 7.24 (d, 1H, J=1.5 Hz), 4.15 (m, 14H), 3.66 (s, 3H), 3.51 (t, 2H, J=5.5 Hz), 2.53 (s, 9H), 2.49 (s, 3H), 2.72 (m, 6H), 1.94 (m, 2H); $^{13}$C NMR (500 MHz, D$_2$O): δ 144.75, 144.60, 144.41, 122.81, 121.75, 121.43, 121.08, 120.59, 58.12, 45.39, 45.17, 45.03, 34.89, 31.24, 29.02, 9.25, 9.13; HRMS (ESI): calculated for $C_{30}H_{48}N_8O_4F_3S$ (M$^{3+}$-3Br) 224.4485; found: 224.4488.

Compound 19 was obtained as a white powder (m.p.: 115-117° C.; Yield: 96%). $^1$H NMR (500 MHz, D$_2$O): δ 7.32-7.28 (m, 6H), 7.23 (s, 1H), 7.20 (s, 1H), 4.10 (m, 14H), 3.62 (s, 3H), 3.47 (t, 2H, J=5.5 Hz), 2.49 (s, 9H), 2.44 (s, 3H), 2.24 (m, 6H), 1.91 (m, 2H); $^{13}$C NMR (400 MHz, D$_2$O): δ 144.60, 144.46, 144.26, 122.70, 121.65, 121.31, 120.95, 120.47, 58.14, 45.46, 45.24, 45.10, 34.98, 34.91, 31.35, 29.18, 9.38, 9.30; HRMS (ESI): calculated for $C_{31}H_{48}N_8O_7F_6S_2$ ($M^{2+}$-2Br) 411.1490; found: 411.1490.

Example 14

Preparation of Compounds 20-23

To a solution of starting material in a mixed solvent system comprising acetonitrile and methanol was added a solution of AgOTf (1 equiv.) in acetonitrile. The resulting mixture was stirred in the dark over a period of 1 hour and filtered to remove the yellow precipitate. The filtrate was rotary evaporated under reduced pressure and the residue washed with diethyl ether followed by drying in vacuo to yield the product.

Compound 21 was obtained as a clear thick oil (Yield: 100%). $^1$H NMR (500 MHz, $D_2O$): δ 7.28 (d, 1H, J=2 Hz), 7.25 (d, 1H, J=2 Hz), 7.23 (d, 1H, J=2.5 Hz), 7.21 (d, 1H, J=2.5 Hz), 4.09 (m, 4H), 3.97 (t, 2H, J=7 Hz), 3.62 (s, 3H), 3.45 (t, 2H, J=6.5 Hz), 2.46 (s, 3H), 2.44 (s, 3H), 2.24 (m, 2H), 1.71 (m, 2H), 1.42 (m, 2H), 1.21 (m, 4H); $^{13}$C NMR (500 MHz, $CD_3CN$): δ 145.19, 144.57, 122.81, 121.69, 121.43, 121.12, 61.42, 48.43, 45.22, 45.15, 35.20, 32.45, 29.67, 29.36, 25.86, 25.27, 9.78; HRMS (ESI): calculated for $C_{19}H_{34}N_4O_4SF_3$ ($M^+$-TfO) 469.2090; found: 469.2097.

Compound 22 was obtained as a clear thick oil (Yield: 100%). $^1$H NMR (400 MHz, $D_2O$): δ 7.27 (m, 2H), 7.26 (d, 1H, J=2.4 Hz), 7.24 (d, 1H, 2.4 Hz), 7.20 (d, 1H, J=2.4 Hz), 7.17 (d, 1H, J=2.4 Hz), 4.06 (m, 10H), 3.59 (s, 3H), 3.44 (t, 2H, J=6 Hz), 2.45 (d, 6H), 2.41 (s, 3H), 2.20 (m, 4H), 1.86 (m, 2H); $^{13}$C NMR (500 MHz, $D_2O$): δ 144.74, 144.57, 144.40, 122.79, 121.74, 121.38, 121.06, 121.02, 120.53, 58.08, 45.37, 45.11, 44.97, 34.81, 31.20, 29.03, 28.99, 9.07, 9.02, 8.94; HRMS (ESI): calculated for $C_{24}H_{37}N_6O_7F_6S_2$ ($M^+$-TfO) 699.2063; found: 699.2065.

Compound 23 (prepared starting from either 18 or 19) was obtained as a white powder (m.p.: 141-143° C.; Yield: 100%). $^1$H NMR (400 MHz, $D_2O$): δ 7.29-7.25 (m, 6H), 7.21 (d, 1H, J=2.0 Hz), 7.18 (d, 1H, J=2.0 Hz), 4.09 (m, 14H), 3.61 (s, 3H), 3.46 (t, 2H, J=5.6 Hz), 2.47 (s, 9H), 2.43 (s, 3H), 2.23 (m, 6H), 1.92 (m, 2H); $^{13}$C NMR (500 MHz, $D_2O$): δ 144.73, 144.57, 122.79, 121.74, 121.39, 121.05, 121.02, 120.53, 58.07, 45.36, 45.08, 44.96, 34.79, 31.20, 28.98, 9.06, 9.01, 8.93; HRMS (ESI): calculated for $C_{31}H_{48}N_8O_7F_6S_2$ ($M^{2+}$-2TfO) 411.1490; found: 411.1488.

General Procedures for Amino Acid Coupling onto Imidazolium Supports

Example 15

Imidazolium Support 20

To a flask comprising imidazolium salt 20 (1.24 g, 4.07 mmol), Boc-Thr(Bzl)-OH (2.28 g, 7.38 mmol) and DMAP (0.10 g, 0.82 mmol) was added dry acetonitrile (16 mL), followed by the addition of a 1.0 M solution of DCC (9.0 mL, 8.99 mmol) in $CH_2Cl_2$. The resulting mixture was stirred over a period of 16 hours and filtered to remove the white precipitate (dicyclohexylurea). The filtrate was rotary evaporated under reduced pressure and the residue washed with diethyl ether followed by drying in vacuo to yield the product 24a as a clear thick oil (2.23 g; Yield: 92%). $^1$H NMR (300 MHz, $CDCl_3$): δ 7.25 (m, 7H), 5.30 (d, 1H, J=8.7 Hz), 4.61 (d, 1H, 11.7 Hz), 4.367 (d, 1H, 11.7 Hz), 4.21-4.03 (m, 6H), 3.79 (s, 3H), 2.54 (s, 3H), 2.10 (m, 2H), 1.45 (s, 9H), 1.30 (d, 3H, 6.3 Hz); $^{13}$C NMR (400 MHz, $CDCl_3$): δ 171.15, 156.31, 144.32, 137.89, 128.63, 128.09, 127.96, 122.80, 121.30, 80.43, 74.35, 70.97, 61.54, 58.78, 45.51, 35.77, 28.84, 28.73, 16.58, 10.06; HRMS (ESI): calculated for $C_{24}H_{36}N_3O_5(C^+)$ 446.2649; found: 446.2651.

Example 16

Imidazolium Supports 21-23

To a flask comprising either of the imidazolium salts 21-23 (1.0 equiv.), amino acid (Boc-Thr(Bzl)-OH; 2 equiv.) and DMAP (0.2 equiv.) was added dry acetonitrile (15 mL/1 g of imidazolium salt), followed by the addition of a 1.0 M solution of DCC (2 equiv.) in $CH_2Cl_2$. The resulting mixture was stirred over a period of 16 hours and filtered to remove the white precipitate (dicyclohexylurea). The filtrate was rotary evaporated under reduced pressure and the residue washed with diethyl ether followed by drying in vacuo to yield a thick oil to which ether was added. The insoluble precipitate was removed by means of phase separation through centrifugation and decantation. The precipitate was subsequently washed with a mixed solvent system comprising ether and ethyl acetate (V/V 1:1), followed by washing with ether. Drying in vacuo yielded either of the products 24b-d.

Compound 24b (derived from imidazolium dimer 21) was obtained as a white powder (m.p.: 44-46° C.; Yield: 83%). $^1$H NMR (400 MHz, $CD_3CN$): δ 7.39-7.28 (m, 9H), 5.50 (d, 1H, J=9.2 Hz), 4.61 (d, 1H, J=11.6 Hz), 4.39 (d, 1H, J=11.6 Hz), 4.23-3.99 (m, 10H), 3.74 (s, 3H), 2.56 (d, 6H), 2.87 (m, 2H), 1.76 (m, 2H), 1.62 (m, 2H), 1.48 (s, 9H), 1.36 (m, 4H), 1.26 (d, 3H, J=6.4 Hz); $^{13}$C NMR (400 MHz, $CD_3CN$): δ 171.15, 156.15, 145.04, 144.42, 138.72, 128.46, 127.78, 127.73, 122.92, 122.82, 121.63, 121.23, 120.91, 79.37, 74.83, 70.70, 65.19, 58.78, 48.50, 45.32, 45.23, 35.26, 29.64, 29.56, 29.40, 28.48, 27.98, 25.83, 25.40, 15.99, 9.73, 9.67; HRMS (ESI): calculated for $C_{34}H_{53}O_5N_5$ ($M^{2+}$-2TfO) 305.7017; found: 305.7017.

Compound 24c (derived from imidazolium trimer 22) was obtained as a white powder (m.p.: 50-52° C.; Yield: 88%). $^1$H NMR (400 MHz, $CD_3CN$): δ 7.40-7.29 (m, 11H), 5.61 (d, 1H, J=8.8 Hz), 4.63 (d, 1H, J=11.6 Hz), 4.41 (d, 1H, J=11.6 Hz), 4.28 (q, 1H, J=8.8 Hz, 2.8 Hz), 4.19-4.05 (m, 13H), 3.73 (s, 3H), 2.62 (s, 3H), 2.56 (s, 3H), 2.54 (s, 3H), 2.30 (m, 4H), 2.07 (m, 2H), 1.45 (s, 9H), 1.28 (d, 3H, J=6 Hz); $^{13}$C NMR (400 MHz, $CD_3CN$): δ 171.07, 156.26, 145.10, 145.03, 144.76, 138.67, 128.52, 127.96, 127.84, 122.79, 121.72, 121.56, 121.38, 120.93, 79.52, 74.62, 70.61, 61.57, 58.79, 54.74, 45.27, 35.20, 29.57, 29.49, 28.51, 27.98, 15.88, 9.74, 9.63, 9.59; HRMS (ESI): calculated for $C_{39}H_{58}O_8N_7F_3S$ ($M^{2+}$-2TfO) 420.7004; found: 420.6999; calculated for $C_{38}H_{58}O_5N_7$ ($M^{3+}$-3TfO) 230.8161; found: 230.8161.

Compound 24d (derived from imidazolium tetramer 23) was obtained as a white powder (m.p.: 92-94° C.; Yield: 83%). $^1$H NMR (500 MHz, $CD_3CN$): δ 7.44-7.29 (m, 13H), 5.62 (d, 1H, J=9 Hz), 4.61 (d, 1H, J=11.5 Hz), 4.40 (d, 1H, J=11.5 Hz), 4.27-4.06 (m, 20H), 3.73 (s, 3H), 2.63 (s, 3H), 2.62 (s, 3H), 2.56 (s, 3H), 2.53 (s, 3H), 2.27 (m, 6H), 2.06 (m, 2H), 1.44 (s, 9H), 1.25 (d, 3H, J=6 Hz); $^{13}$C NMR (400 MHz, $CD_3CN$): δ 171.18, 156.35, 145.15, 145.09, 144.82, 138.72, 128.54, 127.97, 127.85, 122.82, 122.53, 121.74, 121.59, 121.56, 121.39, 120.94, 119.98, 79.46, 74.55, 70.55, 61.43, 58.68, 45.21, 45.18, 45.15, 35.07, 35.05, 30.16, 29.36, 29.27, 29.24, 28.35, 27.79, 15.66, 9.56, 9.44, 9.39; HRMS (ESI): calculated for $C_{46}H_{69}N_9O_8F_3S$ ($M^{3+}$-3TfO) 321.4975; found: 321.4975.

Compound 25 (imidazolium trimer 22 as support) was obtained as a faun powder (m.p.: 214-216° C., decomposition; Yield: 100%). $^1$H NMR (500 MHz, $CD_3CN$): δ 7.73 (s, 1H), 7.59 (s, 1H), 7.45-7.25 (m, 39H), 7.05 (broad), 5.61 (s, 1H), 4.56-4.36 (m, 16H), 4.30 (M, 5H), 4.24-4.04 (m, 20H), 3.95 (m, 1H), 3.83 (m, 1H), 3.72 (m, 9H), 3.65 (m, 2H), 3.52 (m, 2H), 2.56 (s, 3H), 2.53 (s, 3H), 2.51 (s, 3H), 2.25 (m, 4H), 2.06 (m, 2H), 1.37 (s, 9H), 1.34 (d, 3H, J=7.0 Hz), 1.19 (d, 3H, J=6.5 Hz), 1.16 (d, 3H, J=7.0 Hz), 1.14 (m, 3H. J=7.5 Hz), 1.11 (d, 3H, J=6.5 Hz); HRMS (ESI): calculated for $C_{106}H_{138}O_{19}N_{15}$ ($M^{3+}$-3TfO) 641.6759; found: 641.6759.

Compound 26 (imidazolium monomer 20 as support) was obtained as a faun powder (m.p.: 161-163° C.; Yield: 100%). $^1$H NMR (500 MHz, CDCl$_3$): δ 7.40 (s, 2H), 7.30-7.19 (m, 23H), 7.01 (s, 2H), 5.39 (d, 1H, J=4.5 Hz), 4.70 (s, 1H), 4.63 (d, 1H, J=6 Hz), 4.50 (m, 4H), 4.40 (m, 6H), 4.24 (m, 2H), 4.07 (m, 7H), 3.93 (m, 2H), 3.77 (m, 1H), 3.72 (m, 5H), 3.48 (m, 2H), 2.48 (s, 3H), 2.05 (broad, 2H), 1.40 (m, 12H), 1.17 (m, 6H); $^{13}$C NMR (500 MHz, CDCl$_3$): δ 173.34, 172.23, 171.23, 170.87, 170.63, 170.35, 156.46, 144.24, 138.41, 138.06, 138.01, 137.81, 137.21, 128.82, 128.73, 128.54, 128.52, 128.37, 128.23, 127.97, 127.86, 127.81, 127.57, 122.48, 121.93, 81.20, 74.82, 74.11, 73.56, 73.19, 73.04, 71.71, 71.16, 69.87, 68.44, 68.04, 61.27, 59.79, 57.58, 55.68, 55.38, 53.64, 50.68, 45.40, 35.37, 28.44, 28.40, 17.25, 15.56, 16.14, 9.51; HRMS (ESI): calculated for C$_{68}$H$_{87}$O$_{14}$N$_8$ (C$^+$) 1239.6336; found: 1239.6283; calculated for C$_{68}$H$_{88}$O$_{14}$N$_8$ (C$^+$+H$^+$) 620.3204; found: 620.3197.

Compound 26 (imidazolium dimer 21 as support) was obtained as a faun powder (m.p.: 173-175° C.; Yield: 100%). $^1$H NMR (400 MHz, CD$_3$CN): δ 7.50-7.28 (m, 23H), 7.17 (d, 1H, J=8.4 Hz), 5.78 (d, 1H, J=6.4 Hz), 4.57-4.26 (m, 15H), 4.10-3.98 (m, 11H), 3.81-3.71 (m, 7H), 3.60 (m, 2H), 2.51 (s, 6H), 2.21 (m, 2H), 1.73 (m, 2H), 1.59 (m, 2H), 1.40 (s, 9H), 1.30 (m, 7H), 1.18 (m, 6H); $^{13}$C NMR (400 MHz, CD$_3$CN): δ 172.87, 172.14, 171.25, 170.44, 170.30, 169.91, 156.64, 145.04, 144.47, 138.82, 138.70, 138.43, 138.37, 138.08, 128.67, 128.54, 128.48, 127.99, 127.96, 127.94, 127.84, 127.80, 127.71, 122.80, 121.76, 121.18, 120.88, 80.01, 74.64, 74.45, 72.98, 72.93, 72.74, 70.98, 70.52, 69.88, 68.88, 68.61, 64.99, 59.47, 57.11, 55.01, 53.49, 49.70, 48.33, 45.15, 45.06, 35.11, 29.37, 29.15, 28.15, 27.78, 25.43, 25.08, 17.08, 15.86, 15.65, 9.48, 9.39; HRMS (ESI): calculated for C$_{78}$H$_{104}$O$_{14}$N$_{10}$ (M$^{2+}$-2TfO) 702.3861; found: 702.3866.

Compound 26 (imidazolium trimer 22 as support) was obtained as a faun powder (m.p.: 212-214° C., decomposition; Yield: 100%). $^1$H NMR (500 MHz, CD$_3$CN): δ 7.52 (s, 1H), 7.43 (d, 1H, J=5 Hz), 7.37-7.24 (m, 29H), 5.75 (s, 1H), 4.60-4.46 (m, 9H), 4.40 (m, 3H), 4.32-4.21 (M, 3H), 4.12-4.02 (m, 16H), 3.99 (m, 1H), 3.83 (m, 1H), 3.76-3.70 (m, 5H), 3.67 (m, 1H), 3.59 (m, 1H), 3.52 (s, 1H), 2.59 (s, 3H), 2.54 (s, 3H), 2.51 (s, 3H), 2.25 (m, 4H), 2.15-2.06 (m, 2H), 1.41 (s, 9H), 1.32 (d, 3H, J=7 Hz), 1.20 (m, 6H); $^{13}$C NMR (500 MHz, CD$_3$CN): δ 173.16, 172.38, 171.49, 170.50, 170.35, 170.29, 156.58, 145.10, 144.99, 144.80, 138.79, 138.70, 138.44, 138.36, 138.07, 128.68, 128.54, 128.51, 128.01, 127.96, 127.92, 127.89, 127.81, 127.71, 122.90, 122.00, 121.57, 121.23, 120.86, 80.08, 74.62, 74.41, 73.01, 72.93, 72.73, 71.00, 70.63, 69.91, 68.75, 61.44, 59.62, 57.34, 55.34, 53.84, 50.12, 45.25, 45.21, 45.17, 45.13, 35.09, 35.06, 29.30, 29.19, 28.18, 27.82, 17.00, 15.94, 15.60, 9.41, 9.39, 9.32, 9.31; HRMS (ESI): calculated for C$_{82}$H$_{109}$O$_{14}$N$_{12}$ (M$^{3+}$-3TfO) 495.2723; found: 495.2722

Compound 26 (imidazolium tetramer 23 as support) was obtained as a faun powder (m.p.: 213-215° C., decomposition; Yield: 100%). $^1$H NMR (500 MHz, CD$_3$CN): δ 7.53 (s, 1H), 7.43 (s, 1H), 7.35-7.29 (m, 31H), 5.77 (s, 1H), 4.64-4.40 (m, 12H), 4.26 (m, 3H), 4.28-3.99 (m, 20H), 3.83 (m, 1H), 3.73 (m, 4H), 3.68 (m, 2H), 3.60 (m, 1H), 3.50 (m, 1H), 2.59 (s, 3H), 2.58 (s, 3H), 2.54 (s, 3H), 2.51 (s, 3H), 2.27 (m, 6H), 2.08 (m, 2H), 1.41 (s, 9H), 1.32 (d, 3H, J=7 Hz), 1.20 (d, 3H, J=6 Hz); $^{13}$C NMR (400 MHz, CD$_3$CN): δ 173.00, 172.24, 171.35, 170.35, 170.19, 170.15, 156.48, 145.02, 144.92, 144.71, 138.72, 138.62, 138.37, 138.29, 137.98, 128.63, 128.54, 128.49, 128.47, 128.28, 128.02, 127.96, 127.92, 127.88, 127.83, 127.79, 127.76, 127.67, 122.86, 121.97, 121.72, 121.53, 121.20, 120.82, 80.17, 74.70, 74.46, 73.89, 73.10, 73.02, 72.82, 71.09, 70.76, 70.72, 70.00, 68.83, 68.62, 62.18, 61.54, 59.74, 58.02, 57.55, 55.38, 53.98, 50.29, 45.41, 45.34, 45.28, 35.26, 29.49, 29.37, 28.51, 28.38, 28.02, 17.20, 16.16, 15.84, 9.65, 9.56; HRMS (ESI): calculated for C$_{89}$H$_{120}$O$_{14}$N$_{14}$ (M$^{4+}$-4TfO) 402.2271; found: 402.2273.

General Procedure for Peptide Block Coupling

Example 17

Imidazolium Support 22

To a flask comprising imidazolium trimer bound peptide 26 (65.7 mg, 0.034 mmol), hexa-amino-acid peptide 27 (91.8 mg, 0.083 mmol), HBTU (35.9 mg, 0.085 mmol), and HOBT (13.1 mg, 0.085 mmol) was added dry acetonitrile (6 mL), followed by the addition of DIEPA (31 μL, 0.17 mmol). The resulting mixture was stirred over a period of 24 hours under a nitrogen atmosphere and then concentrated by rotary evaporation under reduced pressure. The residue was subsequently combined with ether and transferred to a conical vile. The mixture was subsequently subjected to centrifugation and the top liquid phase decanted. The solid phase was subsequently washed with ether, CH$_2$Cl$_2$, THF, and again with ether. Drying in vacuo yielded product 28 as a faun powder (93.5 mg; Yield: 95%). NMR (500 MHz, CD$_3$CN): δ 7.92 (s, 1H), 7.78 (s, 1H), 7.71 (s, 1H), 7.60 (m, 3H), 7.51 (m, 4H), 7.42-7.20 (m, 38H), 7.20-6.60 (broad, 20H), 5.81 (d, 1H, J=6.4 Hz), 4.57 (m, 4H), 4.53-4.37 (m, 17H), 4.32 (m, 3H), 4.22-4.04 (m, 27H), 3.98 (m, 2H), 3.84-3.68 (m, 14H), 3.62 (m, 3H), 3.59 (m, 2H), 3.46 (m, 2H), 2.55 (s, 3H), 2.53 (s, 3H), 2.51 (s, 3H), 2.24 (m, 2H, overlap), 1.40 (s, 9H), 1.38 (d, 3H, J=8 Hz), 1.32 (d, 3H), 1.20 (m, 6H), 1.56 (m, 6H); HRMS (ESI): calculated for C$_{137}$H$_{173}$O$_{25}$N$_{18}$ (M$^{3+}$-3TfO) 823.4267; found: 823.4262.

To a flask comprising imidazolium trimer bound peptide 25 (51.6 mg, 0.021 mmol), hexa-amino-acid peptide 27 (50.2 mg, 0.045 mmol), HBTU (18.7 mg, 0.049 mmol), and HOBT (6.8 mg, 0.049 mmol) was added dry acetonitrile (15 mL), followed by the addition of DIEPA (21 μL, 0.12 mmol). The resulting mixture was stirred over a period of 24 hours under a nitrogen atmosphere and then concentrated by rotary evaporation under reduced pressure. The residue was subsequently combined with ether and transferred to a conical vile. The mixture was subsequently subjected to centrifugation and the top liquid phase decanted. The solid phase was subsequently washed with ether, CH$_2$Cl$_2$, THF, and again with ether. Drying in vacuo yielded product 29 as a faun powder (70.8 mg; Yield: 99%). HRMS (ESI): calculated for C$_{161}$H$_{202}$O$_{30}$N$_{21}$ (M$^{3+}$-3TfO) 969.8303; found: 969.8291.

General Procedure for Peptide Cleavage from Imidazolium Supports

Example 18

Peptide Cleavage from Imidazolium Support 20-23

To a flask comprising imidazolium bound hexa-amino-acid peptide 26 (1 equiv.) was added a solvent mixture comprising THF and H$_2$O (V/V=3:1) (7 mL/50 mg of support bound peptide 26). The resulting mixture was stirred at room temperature for a few minutes to dissolve the imidazolium bound hexa-amino-acid peptide. An aqueous LiOH (0.1 M, 1 equiv.) or NaOH (0.1 M, 1 equiv.) solution was then added. The resulting mixture was stirred at room temperature over a period of 20 hours and then concentrated by rotary evaporation under reduced pressure. The residue was combined with water and aqueous HCl (0.1M) to adjust the pH to 5. The precipitate was removed by filtration and washed with THF and ether to yield compound 27 as a white powder (m.p.: 167-169° C.; Yield: 81%). [α]$_D^{20}$=33.0 (c=1, in THF); $^1$H NMR (500 MHz, CD$_3$COCD$_3$): 7.75 (s, 1H), 7.70 9s, 1H), 7.62 (d, 1H, J=7.5 Hz), 7.51 (d, 1H, J=7.0 Hz), 7.42 (d, 1H, J=9.0 Hz), 7.35-7.21 (m, 20H), 6.11 (d, 1H, J=7.5 Hz), 4.73 (m, 1H), 4.63-4.43 (m, 15H), 4.23 (m, 2H), 4.10 (s, 1H), 3.86 (m, 3H), 3.73 (m, 1H), 3.67 (m, 1H), 3.60 (m, 1H), 1.40 (s, 9H), 1.30 (d, 3H, J=7.0 Hz), 1.21 (m, 6H); $^{13}$C NMR (500 MHz, THF-d$^4$, concentrated): δ 174.18, 173.87, 172.31, 170.93, 171.10, 157.77, 141.15, 140.55, 130.02, 129.96, 129.87, 129.50, 129.08, 128.96, 80.42, 77.61, 74.77, 74.68, 73.25, 72.85, 72.48, 72.17, 60.68, 58.98, 55.53, 55.00, 54.89, 50.75, 29.78, 20.56, 18.12, 17.61; HRMS (ESI): calculated for $C_{60}H_{75}O_{14}N_6$ (M+H$^+$) 1103.5335, found: 1103.5313.

General Procedure for Recovering the Imidazolium Supports Following Cleavage of the Peptide Products Example 19

Imidazolium Support 20-23

Following filtration to remove the peptide, the aqueous phase was collected and the water removed by means of freeze drying. The solid was then combined with acetonitrile and the resulting mixture filtered to remove insoluble inorganic salts. The organic phase was then removed by means of rotary evaporation under reduced pressure and the residue washed with diethyl ether followed by drying in vacuo to yield the imidazolium support. The recovered imidazolium supports exhibited $^1$H-NMR and $^{13}$C NMR spectra similar to freshly prepared material.

REFERENCES 1. a) Merrifield, R. B. Solid Phase Peptide Synthesis. I. The Synthesis of a Tetrapeptide. *J. Am. Chem. Soc.* 1963, 85, 2149-2154. (b) Seeberger, P. H.; Haase, W. C. *Chem. Rev.* 2000, 100, 4349-4394.
2. Bayer, E., Mutter, M. (1972) Liquid phase synthesis of peptides. *Nature*, 237, 512-513.
3. a) Mutter, M.; Hagenmaier, H.; Bayer, E. *Angew. Chem. Int. Ed.* 1971, 10, 811-812; b) Bayer, E.; Mutter, M. *Nature* 1972, 237, 512-513.
4. For reviews, see: a) Gravert, D. J.; Janda, K. D. Soluble Polymer-Supported Organic Synthesis; *Chem. Rev.* 1997, 97, 489-509; b) Toy, P. H.; Janda K. D., *Acc. Chem. Res.* 2000, 33, 546-554.
5. (a) Horvath, I. T.; Rabai, *J. Science* 1994, 266, 72-75; (b) Studer, A.; Hadida, S.; Ferritto, R.; Kim, S.-Y.; Jeger, P.; Wipf, P.; Curran, D. P. Fluorous Synthesis: A Fluorous Phase Strategy for Improving Separation Efficiency in Organic Synthesis. *Science* 1997, 275, 823-826; (c) Horvath, I. T. Fluorous Bipliase Chemistry. *Acc. Chem. Res.* 1998, 31, 641-650; (d) Wende, M.; Meier, R.; Gladysz, J. A. *J. Am. Chem. Soc.* 2001, 123, 11490-11491; (e) Wende, M.; Gladysz, J. A. *J. Am. Chem. Soc.* 2003, 125, 5861-5872; (f) Zhang, W. *Tetrahedron* 2003, 59, 4475; and *Chem. Rev.* 2004, 104, 2531-2556. (g) Betzemeier, B.; Knochel, P. *Angew. Chem., Int. Ed. Engl.,* 1997, 36, 2623-2624.
6. a) Curran, D. P.; Ferrito, R.; Hua, Y. *Tetrahedron Lett.* 1998, 39, 4937. b) Miura, T.; Goto, K.; Hosaka, D.; Inazu, T. Oligosaccharide Synthesis on a Fluorous Support. *Angew. Chem. Int. Ed.* 2003, 42, 2047-2051. c) Miura, T.; Hirose, Y.; Ohmae, M.; Inazu, T. *Org. Lett.* 2001, 3, 3947. d) Miura, T.; Inazu, T. *Tetrahedron Lett.* 2003, 44, 1819. e) Jing, Y. Huang, X. *Tetrahedron Lett.* 2004, 45, 4615. f) Manzoni, L. *Chem. Comm.* 2003, 2930. g) Manzoni, L.; Castelli, R. *Org. Lett.* 2004, 6, 4195. h) Palmacci, E. R.; Hewitt, M. C.; Seeberger, P. H. *Angew. Chem. Int. Ed.* 2001, 40, 4433.
7. a) Mizuno, M.; Goto, K.; Miura, T.; Hosaka, D.; Inazu, T. *Chem. Commun.* 2003, 972-973; b) Mizuno, M.; Goto, K.; Miura, T.; Matsuura, T.; Inazu, T. Peptide Synthesis on Fluorous Support. *Tetrahedron Lett.* 2004, 45, 3425-3428.
8. For recent reviews on ionic liquids, see: a) Wasserscheid, P.; Keim, W. *Angew. Chem. Int. Ed.* 2000, 39, 3773. b) Welton, T. *Chem. Rev.* 1999, 99, 2071. c) Sheldon, R. *Chem. Comm.* 2001, 2399. d) Wilkes, J. S. *Green Chem.* 2002, 4, 73; e) Wasserscheid, P.; Welton, T. Ionic Liquids in Synthesis, Wiley-VCH, Weinheim, Germany, 2003; (f) Holbrey, J. D., Seddon, K. R. *J. Chem. Soc., Dalton Trans.* 1999, 2133-2140; (g) Wilkes, J. S. *J. Mol. Cat.* A: Chem. 2004, 214, 11-17; (h) Gordon, C. M. *Appl. Catal. A* 2001, 222, 101-107; (i) Zhao, D.; Wu, N C; Kou, Y.; Min, E. *Catal. Today* 2002, 74, 157-189; (j) Dupont, J. de Souza, R. F. Suarez, P. A. Z. *Chem. Rev.* 2002, 102, 3667-3692; (k) Jain, N; Kumar, A. Chauhan, S. M. *Tetrahedron* 2005, 61, 1015-1060.
9. a) Fukumoto, K.; Yoshizawa, M.; Ohno, H. *J. Am. Chem. Soc.* 2005, 127, 2398-2399. b) Nakajima, H.; Ohno, H. *Polymer* 2005, 46, 11499-11504.
10. a) Xu, J.; Yang, J.; NuLi, Y.; Wang, J.; Zhang, Z. *J. Power Sources* 2006, 160, 621-626. b) Galinski, M.; Lewandowski, A.; Stepniak, I. *Electrochim. Acta* 2006, 51, 5567-5580.
11. Marcilla, R.; Alcaide, F.; Sardon, H.; Pomposo, J. A.; Pozo-Gonzalo, C.; Mecerreyes, D. *Electrochem. Commun.* 2006, 8, 482-488.
12. Anderson, J. L.; Armstrong, D. W.; Wei, G.-T. *Anal. Chem.* 2006, 78, 2893-2902.
13. a) Audic, N.; Clavier, H.; Mauduit, M.; Guillemin, J.-C. *J. Am. Chem. Soc.* 2003, 125, 9248-9249. b) Yao, Q.; Zhang, Y. Angew. Chem. Int. Ed. 2003, 42, 3395-3398. c) Lee, A.; Zhang, Y.; Piao, J.; Yoon, H.; Song, C.; Choi, J.; Hong, J. *Chem. Commun.* 2003, 2624-2625. d) Zhao, D.; Fei, Z.; geldbach, T. J.; Scopelliti, R.; Dyson, P. 3. *J. Am. Chem. Soc.* 2004, 126, 15876-15882.
14. a) Wu, X.-E.; Ma, L.; Ding, M.-X.; Gao, L.-X. *Synlett* 2005, 4, 607-610. b) Mi, X.; Luo, S.; Cheng, J.-P. *J. Org. Chem.* 2005, 70, 2338-2341.
15. a) Fraga-Dubreuil, J.; Bazureau, J. P. *Tetrahedron Lett.* 2001, 42, 6097-6100. b) He, X.; Chan, T. H. *Synthesis,* 2006, 10, 1645-1651. c) He, X.; Chan, T. H. Tetrahedron, 2006, 62, 3389-3394. d) Miao, W.; Chan, T. H.; *Org. Lett.* 2003, 5, 5003-5005. e) Miao, W.; Chan, T. H. *J. Org. Chem.* 2005, 70, 3251-3255. f) Qian, W.; Jin, E.; Bao, W.; Zhang, Y. *Angew. Chem. Int. Ed.* 2005, 44, 952-955. g) For review, see Miao, W.; Chan, T. H. *Acc. Chem. Res.,* 2006, 39, 897-908. h) For reviews on physical and chemical properties of ionic liquids, see: a) Chiappe, C.; Pieraccini, D. *J. Phys. Org. Chem.* 2005, 18 275-297. b) Handy, S. T. *Curr. Org. Chem.* 2005, 9, 959-988.
16. a) Sheldon, R. *Chem. Commun.* 2001, 2399-2407; b) Sheldon, R. A.; Lau, R. M.; Sorgedrager, M. J.; Rantwijk, F. V.; Seddon, K. R. Biocatalysis in Ionic Liquids. *Green Chem.* 2002, 4, 147-151.
17. a) Fuller, J.; Carlin, R. T., Osteryoung, R. A. *J. Electrochem. Soc.* 1997, 144, 3881-3886; b) Fuller, J.; Breda, A. C., Carlin, R. T. (1998) *J. Electroanal. Chem.,* 1998, 459, 29-34.
18. a) Huddleston, J. G., Rogers, R. D. *Chem. Commun.* 1998, 1765-1766; b) Boesmann, A., Datsevich, L., Jess, A., Lauter, A., Schmitz, C., Wasserscheid, P. *Chem. Commun.* 2001, 2494-2495.
19. Ye, C., Liu, W., Chen, Y., Yu, L. *Chem. Commun.* 2001, 2244-2245.
20. a) Kimizuka, N.; Nakashima, T. Spontaneous Self-Assembly of Glycolipid Bilayer Membranes in Super-Phylic Ionic Liquid and Formation of Ionogel. *Langmuir* 2001, 17, 6759-6761; b) For other ionic liquids containing PEG, see Leone, A. M.; Weatherly, S. C.; Williams, M. E.; Thorp, H. H.; Murray, R. W. *J. Am. Chem. Soc.* 2001, 123, 218-222.

21. a) Fraga-Dubreuil, J.; Bazureau, J. P. *Tetrahedron Lett.* 2001, 42, 6097-6100; b) Fraga-Dubreuil, J.; Bazureau, J. P. *Tetrahedron* 2003, 59, 6121-6130; c) Handy, S. T.; Okello, M. *Tetrahedron Lett.* 2003, 44, 8399-8402; d) Miao, W.; Chan, T. H. *Org. Lett.* 2003, 5, 5003-5005; e) Anjaiah, S.; Chandrasekhar, S.; R. Gree, *Tetrahedron Lett.* 2004, 45, 569-571; f) de Kort, M.; Tuin, A. W.; Kuiper, S.; Overkleeft, H. S.; van der Marel, G. A.; Buijsman, R. C. *Tetrahedron Lett.* 2004, 45, 2171-2175; g) Law, M. C.; Wong, K.-Y.; Chan, T. H. J. Org. Chem. 2005, 70, 10434.
22. Peptide synthesis using ionic liquids as reaction media has been reported. See: Vallette, H.; Ferron, L.; Coquerel, G.; Gaumont, A.-C.; Plaquevent, J.-C. *Tetrahedron Lett.* 2004, 45, 1617-1619.
23. Bower, J. D.; Guest, K. P.; Morgan, B. A. *J. Chem. Soc. Perkin Trans.* 1, 1976, 2488.
24. Miao, W.; Chan, T. H. *J. Org. Chem.* 2005, 70, 3251.
25. He, X.; Chan, T. H. Synthesis 2006, 1645-1651.
26. Donga, R. A.; Khaliq-Uz-Zaman, S. M.; Chan, T.-H.; Damha, M. J. *J. Org. Chem.* 2006, 71, 7907-7910.
27. a) Lozano P.; Martinez-Sanchez M. *J. Coll. Interf. Sci.* 2004, 280, 149-154. b) Zhao, F.; Wu, X.; Wang, M.; Liu, Y.; Gao, L.; Dong, S. *Anal. Chem.* 2004, 76, 4960-4967. c) US Appl. 2005106440 (Komiya).
28. a) Xu, J.; Yang, J.; NuLi, Y.; Wang, J.; Zhang, Z. *J. Power Sources* 2006, 160, 621-626. b) Galinski, M.; Lewandowski, A.; Stepniak, I. *Electrochim. Acta* 2006, 51, 5567-5580.
29. a) Sekhon, S. S.; Lalia, B.-S.; Park, J.-S.; Kim, C.-S.; Yamada, K. *J. Mater. Chem.* 2006, 16, 2256-2265. b) Lalia, B. S.; Sekhon, S. S. *Chem. Phys. Lett.* 2006, 425, 294-300. c) Kosmulski, M.; Szafran, M.; Saneluta, C.; Marczewska-Boczkowska, K. *J. Coll. and Interf Sci.* 2005, 291, 214-217. d) Kudo, K.; Mitsushima, S.; Kamiya, N.; Ota, K.-I. *Electrochemistry* 2005, 73, 668-674. e) Hagiwara, R.; Nohira, T.; Matsumoto, K.; Tamba, Y. *Electrochem. Sol.-Stat. Lett.* 2005, 8, A231-A233. f) Li, Z.; Liu, H.; Liu, Y.; He, P.; Li, J. *J. Phys. Chem. B* 2004, 108, 17512-17518.
30. a) Seki, S.; Kobayashi, Y.; Miyashiro, H.; Ohno, Y.; Usami, A.; Mita, Y.; Kihira, N.; Watanabe, M.; Terada, N. *J. Phys. Chem. B* 2006, 110, 10228-10230. b) Abu-Lebdeh, Y.; Abouimrane, A.; Alarco, P.-J.; Armand, M. *J. Power Sources* 2006, 154, 255-261. c) Seki, S.; Kobayashi, Y.; Miyashiro, H.; Ohno, Y.; Usami, A.; Mita, Y.; Watanabe, M.; Terada, N. *Chem. Commun.* 2006, 544-545. d) Byrne, N.; Howlett, P. C.; MacFarlane, D. R.; Forsyth, M. *Adv. Mater.* 2005, 17, 2497-2501. e) Nakagawa, H.; Izuchi, S.; Kuwana, K.; Nukuda, T.; Aihara, Y. *J. Electrochem. Soc.* 2003, 150, A695-A700.
31. a) Wang, P.; Wenger, B.; Humphry-Baker, R.; Moser, J.-E.; Teuscher, J.; Kantlehner, W.; Mezger, J.; Stoyanov, E. V.; Zakeeruddin, S. M.; Graetzel, M. *J. Am. Chem. Soc.* 2005, 127, 6850-6856. b) For review, see: Matsumoto, H.; Matsuda, T. *Electrochemistry* 2002, 70, 190-194.
32. a) Kato, T.; Kado, T.; Tanaka, S.; Okazaki, A.; Hayase, S. *J. Electrochem. Soc.* 2006, 153, A626-A630. b) Mazille, F.; Fei, Z.; Kuang, D.; Zhao, D.; Zakeeruddin, S. M.; Graetzel, M.; Dyson, P. *J. Inorg. Chem.* 2006, 45, 1585-1590. c) Kawano, R.; Watanabe, M. *Chem. Commun.* 2005, 2107-2109. d) Wang, P.; Zakeeruddin, S. M.; Humphry-Baker, R.; Graetzel, M. *Chem. Mater.* 2004, 16, 2694-2696.
33. a) Yu, L.; Garcia, D.; Ren, R.; Zeng, X. *Chem. Commun.* 2005, 2277-2279. b) Liang, C.; Yuan, C.-Y.; Warmack, R. J.; Barnes, C. E.; Dai, S. *Anal. Chem.* 2002, 74, 2172-2176.
34. For reviews on cellulose in ionic liquids, see: a) Zhu, S.; Wu, Y.; Chen, Q.; Yu, Z.; Wang, C.; Jin, S.; Ding, Y.; Wu, G. *Green Chem.* 2006, 8, 325-327. b) Holbrey, J. D.; Chen, J.; Turner, M. B.; Swatloski, R. P.; Spear, S. K.; Rogers, R. D. *ACS Symposium Series* 2005, 913 71-87.
35. a) Fortunato, R.; Branco, L. C.; Afonso, C. A. M.; Benavente, J.; Crespo, J. G. *J. Membr. Sci.* 2006, 270, 42-49. b) Coll, C.; Labrador, R. H.; Manez, R. Martinez; Soto, J.; Sancenon, F.; Segui, M.-J.; Sanchez, E. *Chem. Commun.* 2005, 24, 3033-3035. c) For reviews, see: a) Schaefer, T.; Branco, L. C.; Fortunato, R.; Izak, P.; Rodrigues, C. M.; Afonso, C. A. M.; Crespo, J. G. *ACS Symposium Series* 2005, 902, 97-110. b) Scovazzo, P.; Visser, A. E.; Davis, J. H., Jr.; Rogers, R. D.; Koval, C. A.; D., Dan L.; N., Richard D. *ACS Symposium Series* 2002, 818, 69-87.
36. Wang, Y.; Yang, H. *J. Am. Chem. Soc.* 2005, 127, 5316-5317.
37. a) Zhang, J.; Zhang, S.; Dong, K.; Zhang, Y.; Shen, Y.; Lu, X. *Chem. Eur. J.* 2006, 12, 4021-4026. b) Tang, J.; Sun, W.; Tang, H.; Radosz, M.; Shen, Y. *Macromolecules* 2005, 38, 2037-2039. c) Zhang, S.; Chen, Y.; Li, F.; Lu, X.; Dai, W.; Mori, R. *Catal. Today* 2006, 115, 61-69. d) Bates, E. D.; Mayton, R. D.; Ntai, I.; Davis, J. H., Jr. *J. Am. Chem. Soc.* 2002, 124, 926-927.
38. Anderson, J. L.; Armstrong, D. W.; Wei, G.-T. *Anal. Chem.* 2006, 78, 2893-2902.
39. (a) Berthod, A.; Ruiz-Angel, M. J.; Huguet, S. *Anal. Chem.* 2005, 77, 4071-4080. b) Qin, W.; Wei, H.; Li, S. F. Y. *J. Chromatogr. A* 2003, 985, 447-454.
40. a) Tholey, A.; Heinzle, E. *Anal. Bioanal. Chem.* 2006, 386, 24-37. b) Bardi, U.; Chenakin, S. P.; Lavacchi, A.; Pagura, C.; Tolstogouzov, A. *Appl. Surf Sci.* 2006, 252, 7373-7382. c) Henderson, M. A.; McIndoe, J. S. *Chem. Commun.* 2006, 2872-2874.
41. a) Ouadi, A.; Gadenne, B.; Hesemann, P.; M., J. J. E.; Billard, I.; Gaillard, C.; Mekki, S.; Moutiers, G. *Chem. Eur. J.* 2006, 12, 3074-3081. b) Dietz, M. L.; Stepinski, D. C. *Green Chem.* 2005, 7, 747-750. c) Visser, A. E.; Swatloski, R. P.; Reichert, W. M.; Mayton, R.; Sheff, S.; Wierzbicki, A.; Davis, J. H.; Rogers, R. D., Jr. *Environ. Sci. Technol.* 2002, 36, 2523.
42. The thermogravimetric analysis (TGA) was performed on a TGA Q500 from TA instruments. The running method used was ramped from 25° C. to 550° C., 20° C./min, under nitrogen, switching to air and then ramped at 20° C./min to 700° C. The type of pan used was platinum.
43. Dziadek, S.; Brocke, C.; Kunz, H. *Chem. Eur. J.* 2004, 10, 4150-4162.
44. Danishefsky, S. J.; Allen, J. R. Angew. Chem. Int. Ed. 2000, 39, 836-863.
45. The HPLC apparatus was equipped with a reverse phase $C_{18}$ column (Agilent Zorbax Extend-C18, 4.6×250 mm). The elution was performed using a linear gradient from 50% to 100% of B in A over 20 min, followed by a linear gradient elution from 100% to 50% of B in A over 10 min, where A was $H_2O$/0.05% TFA (v/v) and B was $CH_3CN$/0.05% TFA (v/v), at a flow rate of 0.8 mL/min. UV absorbance was detected at 210 nm.

What is claimed is:

1. An imidazolium-type ionic oligomer of the formula:

wherein:
n is an integer ranging from 1 to 20;
A is N or m is an integer ranging from 1 to 5;
X is selected from the group consisting of Br, OTf, $CF_3CO_2$, $CH_3CO_2$, $BF_4$, $PF_6$, $NTf_2$, F, Cl and I; and
R is selected from the group consisting of hydrogen and $C_{1-10}$ alkyl.

2. The imidazolium-type ionic oligomer of claim 1, wherein the formula is:

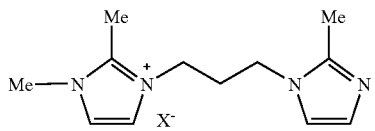

wherein X is selected from the group consisting of Br and TfO.

3. The imidazolium-type ionic oligomer of claim 1, wherein the formula is:

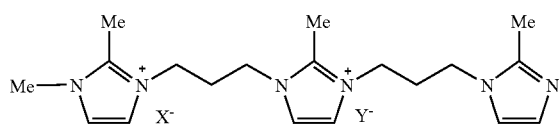

wherein X and Y are independently selected from the group consisting of Br and TfO.

4. The imidazolium-type ionic oligomer of claim 1, wherein the formula is:

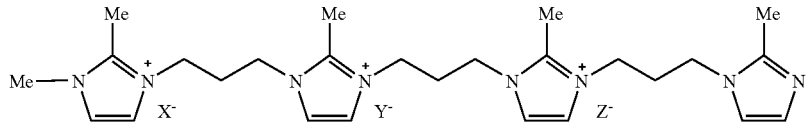

wherein X, Y and Z are independently selected from the group consisting of Br and TfO.

5. The imidazolium-type ionic oligomer of claim 1, wherein the formula is:

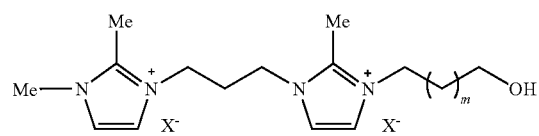

wherein:
X is selected from the group consisting of Br and TfO; and
m is an integer ranging from 1 to 5.

6. The imidazolium-type ionic oligomer of claim 1, wherein the formula is:

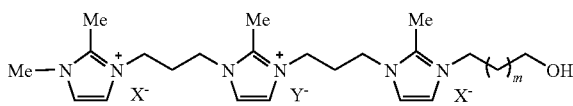

wherein:
X and Y are independently selected from the group consisting of Br and TfO; and
m is an integer ranging from 1 to 5.

7. The imidazolium-type ionic oligomer of claim 1, wherein the formula is:

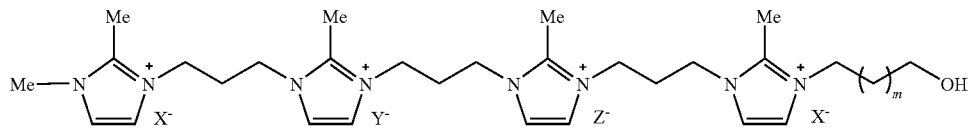

wherein:
X, Y and Z are independently selected from the group consisting of Br and TfO; and
m is an integer ranging from 1 to 5.

8. A method for preparing an oligopeptide, the method comprising:
a) contacting a first suitably protected amino acid with an imidazolium-type oligomer of the formula:

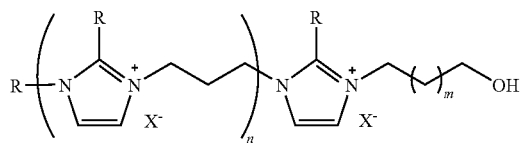

wherein:
n is an integer ranging from 1 to 20;
m is an integer ranging from 1 to 5;
X is selected from the group consisting of Br, OTf, $CF_3CO_2$, $CH_3CO_2$, $BF_4$, $PF_6$, $NTf_2$, F, Cl and I; and
R is selected from the group consisting of hydrogen and $C_{1-10}$ alkyl;
to provide an oligomer bound amino acid; and
b) reacting said oligomer bound amino acid with a second suitably protected amino acid.

9. The method of claim 8, further comprising:
c) repeating step b) to provide an oligomer-bound oligopeptide; and
d) isolating the oligopeptide.

10. The method of claim 8, wherein the imidazolium-type oligomer is formula:

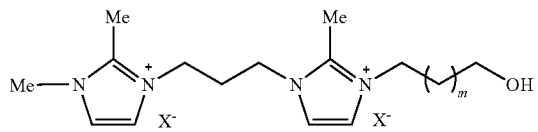

wherein:
X is selected from the group consisting of Br and TfO; and
m is an integer ranging from 1 to 5.

11. The method of claim 8, wherein the imidazolium-type oligomer is formula:

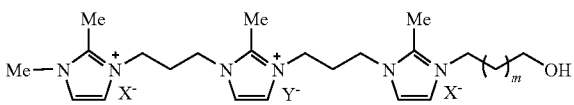

wherein:
X and Y are independently selected from the group consisting of Br and TfO; and
m is an integer ranging from 1 to 5.

12. The method of claim 8, wherein the imidazolium-type oligomer is formula:

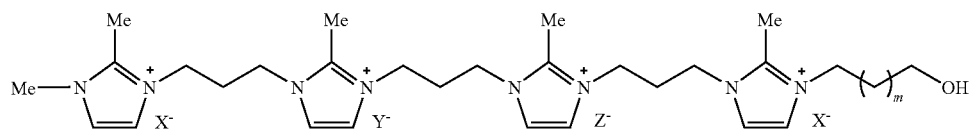

wherein:
X, Y and Z are independently selected from the group consisting of Br and TfO; and
m is an integer ranging from 1 to 5.

13. A kit comprising:
(a) at least one imidazolium-type ionic oligomer as defined in claim 1; and
(b) at least one amino acid.

14. An article of manufacture comprising:
(a) at least one imidazolium-type ionic oligomer as defined in claim 1; and
(b) at least one amino acid.

* * * * *